United States Patent
Boyle et al.

(10) Patent No.: US 7,202,244 B2
(45) Date of Patent: Apr. 10, 2007

(54) CHK-1 INHIBITORS

(75) Inventors: Robert George Boyle, Cambridge (GB); Hassan Julien Imogai, Cambridge (GB); Michael Cherry, Suffolk (GB)

(73) Assignee: Millennium Pharmaceuticals, Inc., Cambridge, MA (US)

( * ) Notice: Subject to any disclaimer, the term of this patent is extended or adjusted under 35 U.S.C. 154(b) by 0 days.

(21) Appl. No.: 10/446,627

(22) Filed: May 28, 2003

(65) Prior Publication Data

US 2004/0014765 A1     Jan. 22, 2004

Related U.S. Application Data

(60) Provisional application No. 60/384,207, filed on May 29, 2002, provisional application No. 60/432,796, filed on Dec. 12, 2002.

(51) Int. Cl.
*A01N 43/58* (2006.01)
*A61K 31/50* (2006.01)
*C07D 241/00* (2006.01)

(52) U.S. Cl. ...................... 514/247; 544/224; 544/336; 544/358

(58) Field of Classification Search ................ 514/224; 544/224, 336, 358
See application file for complete search history.

(56) References Cited

FOREIGN PATENT DOCUMENTS

| EP | 1 153 920 A1 | 11/2001 |
| EP | 1 199 306 A1 | 4/2002 |
| WO | WO 02/070494 | * 9/2002 |
| WO | WO 02/070494 A1 | 9/2002 |

OTHER PUBLICATIONS

Jackson, J. R., et al., "An Indolocarbazole Inhibitor of Human Checkpoint Kinase (Chk1) Abrogates Cell Cycle Arrest Caused by DNA Damage", *Cancer Research*, 60: 566-572 (2000).

* cited by examiner

*Primary Examiner*—James O. Wilson
*Assistant Examiner*—Paul V. Ward
(74) *Attorney, Agent, or Firm*—Hamilton, Brook, Smith & Reynolds, PC

(57) ABSTRACT

Disclosed are novel inhibitors of Chk-1 and methods of using the same for therapy.

7 Claims, No Drawings

CHK-1 INHIBITORS

RELATED APPLICATIONS

This application claims the benefit of U.S. Provisional Application No. 60/384,207, filed May 29, 2002, and U.S. Provisional Application No. 60/432,796, filed Dec. 12, 2002. The entire teachings of these two applications are incorporated herein by reference.

BACKGROUND OF THE INVENTION

Cell cycle checkpoints are regulatory pathways that control the order and timing of cell cycle transitions. They ensure that critical events such as DNA replication and chromosome segregation are completed in high fidelity. The regulation of these cell cycle checkpoints is a critical determinant of the manner in which tumor cells respond to many chemotherapies and radiation. Many effective cancer therapies work by causing DNA damage; however, resistance to these agents remains a significant limitation in the treatment of cancer. Of the several mechanisms of drug resistance, an important one is attributed to the prevention of cell cycle progression through the control of critical activation of a checkpoint pathway. This arrests the cell cycle to provide time for repair, and induces the transcription of genes to facilitate repair, thereby avoiding immediate cell death. By abrogating checkpoint arrests at, for example, the G2 checkpoint, it may be possible to synergistically augment tumor cell death induced by DNA damage and circumvent resistance. Human Chk-1 plays a role in regulating cell cycle arrest by phosphorylating the phosphatase cdc25 on Serine 216, which may be involved in preventing activation of cdc2/cyclin B and initiating mitosis. Therefore, inhibition of Chk-1 should enhance DNA damaging agents by initiating mitosis before DNA repair is complete and thereby causing tumor cell death.

SUMMARY OF THE INVENTION

It has now been found that certain diaryl ureas are effective inhibitors of Chk-1. For example, the compounds shown in Table 1 of Example 37 have an $IC_{50}$ less than 20 μmol when tested in an in vitro assay that assesses the inhibitory activity of test compounds. It has also been found that phenyl urea CHK-1 inhibitors substituted ortho to the urea nitrogen with an $-X-NH_2$ group, wherein X is an inert linking group, are significantly more effective in enhancing the cytotoxicity of DNA damaging agents than other CHK-1 inhibitors (see Example 38). Linking groups whose length corresponds to the length of $-O-(C_{2-5}$ alkylidene)- are particularly efficacious. Based on these discoveries, novel Chk-1 inhibitors, methods of inhibiting Chk-1 in a subject and methods of treating cancer are disclosed herein.

One embodiment of the present invention is a method of inhibiting Chk-1 in a subject in need of such treatment. The method comprises administering to the subject an effective amount of a compound of Formula I:

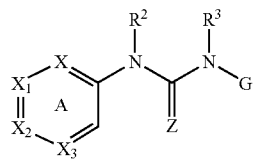

The variables in Formula (I) are defined below.

X is N or $CR^1$. In one preferred embodiment, X is $C-T-NH_2$, $C-V-T-NH_2$, $C-T-NHR^x$ or $C-V-T-NHR^x$.

$X_1-X_3$ are independently CH or N, provided that $X_1-X_3$ are not all N and X, $X_1$ and $X_2$ are not all N.

Z is O, S, or N—CN.

Ring A is optionally substituted at any substitutable carbon by $R^4$. Preferably, Ring A is a phenyl ring optionally substituted at any substitutable carbon by $R^4$.

$R^1$ is —H, halogen, $T-R^6$ or $V-T-R^6$, or $R^1$ and $R^2$ taken together with their intervening atoms form a 5–7 membered ring, preferably a 5–7 membered heterocycle. When $R^1$, $R^2$ and their intervening carbons together form a heterocycle, preferred values for $R^1$ and $R^2$ together include an optionally substituted methylene, ethylene and propylene. Suitable substituents are as defined below for an alkylidine group. Preferred substituents are =O, $C_{1-3}$ aliphatic, amine $[N(R^8)_2]$ and amino alkyl $[(CH_2)_qN(R^8)_2]$. Each $R^8$ is independently $C_{1-6}$ alkyl or, taken together with the nitrogen atom to which they are bonded, is a 5–7 membered nitrogen-containing heterocycle; and q is an integer from 1–6.

T is a $C_{1-6}$ straight or branched alkylidene chain that is optionally interrupted by —O—, —S—, —N($R^5$)—, —S(O)—, —SO_2—, —C(O)—, —OC(O)—, —N($R^5$)C(O)—, —C(O)N($R^5$)—, —SO_2N($R^5$)—, or —N($R^5$)SO_2—, wherein the alkylidene chain or a portion thereof is optionally part of a 3–6 membered ring system.

V is —O—, —S—, —N($R^5$)—, —S(O)—, —SO_2—, —C(O)—, —OC(O)—, —N($R^5$)C(O)—, —C(O)N($R^5$)—, —SO_2N($R^5$)—, or —N($R^5$)SO_2—.

$R^2$ and $R^3$ are each independently selected from hydrogen, $C_{1-6}$ alkyl optionally substituted with an amine $[N(R^8)_2]$, —C(=O)R, —CO_2R, or SO_2R, or $R^2$ and $R^3$ taken together with their intervening atoms form an optionally substituted 5–6 membered ring, preferably a 5–6 membered heterocycle. When $R^2$, $R^3$ and the intervening carbons together form a 5–6 membered heterocycle, $R^2$ and $R^3$ together form, for example, an optionally substituted ethylene, propylene or $CH_2NHCH_2$. Suitable substituents for the carbon atoms in the groups formed by $R^2$ and $R^3$ are as defined below for an alkylidine group and preferred substituents are =O, $C_{1-3}$ alkyl, amine $[N(R^8)_2]$ and amino alkyl $[(CH_2)_qN(R^8)_2]$; and suitable substituents for the nitrogen atom in the groups formed by $R^2$ and $R^3$ are as defined below for the nitrogen atom of a heterocycle. $R^8$ and q are defined above.

Each $R^4$ is independently selected from halo, —OR, —SR, —CN, —NO_2, —N($R^5$)_2, —N($R^5$)C(O)R, —N($R^5$)CO_2R, —N($R^5$)C(O)N($R^5$)_2, —C(O)N($R^5$)_2, —OC(O)N($R^5$)_2, —CO_2R, —SO_2R, —S(O)R, —SO_2N($R^5$)_2, —N($R^5$)SO_2R, or an optionally substituted group selected from $C_{1-8}$ aliphatic, aryl, aralkyl, heterocycle, heterocyclealkyl, heteroaryl, or heteroaralkyl. Additionally, $R^4$ can be —C(O)$R^5$.

Additionally, two $R^4$s ortho to each other, taken together with the carbon atoms of Ring A to which they are bonded, form an optionally substituted five or six membered phenyl, pyridyl or heterocycle fused to Ring A. When two ortho $R^4$s and the carbon atoms of Ring A to which they are bonded form a heterocycle, the two ortho $R^4$s, together form, for example, an optionally substituted propylene, butylene, methylene dioxy, ethylene dioxy, $O(CH_2)_2$ $O(CH_2)_3$, $NH(CH_2)_2$ or $NH(CH_2)_3$. Suitable substituents for the groups formed by two $R^4$ groups are as described below for heterocycles.

In another alternative, $R^1$ and an $R^4$ ortho to $R^1$, taken together with the carbon atoms of Ring A to which they are bonded, form an optionally substituted five or six membered heterocycle fused to Ring A. When $R^1$, an ortho $R^4$ and the carbon atoms of Ring A to which they are bonded together form a heterocycle, $R^1$ and the ortho $R^4$ taken together form, for example, an optionally substituted propylene, butylene, methylene dioxy, ethylene dioxy, $O(CH_2)_2$ $O(CH_2)_3$, $NH(CH_2)_2$ or $NH(CH_2)_3$. Suitable substituents are as described below for heterocycles. Preferred substituents are $C_{1-3}$ alkyl, amine $[N(R^8)_2]$ and amino alkyl $[(CH_2)_qN(R^8)_2]$. $R^8$ and q are as described above.

Each $R^5$ is independently selected from hydrogen, $C_{1-6}$ aliphatic, $-CO_2R$, $-SO_2R$, or $-C(O)R$, or two $R^5$s on the same nitrogen taken together with the nitrogen form a 5–8 membered heteroaryl or heterocycle ring having 1–4 heteroatoms selected from N, O or S.

$R^6$ is hydrogen, $-OR$, $-N(R)_2$, or an optionally substituted 4–14 membered ring system wherein at least one of the ring atoms is a basic nitrogen. Preferred ring systems for $R^6$ include cycloalkyl, heteroaryl and monocyclic heterocyclyls formed from $-N(R)_2$, taken together. Suitable substituents for ring systems represented by $R^6$ are as described below for aliphatics, heteroaryls and hetercyclyls. Preferred substituents are amine $[N(R^8)_2]$ and amino alkyl $[(CH_2)_qN(R^8)_2]$. $R_8$ and q are as described above.

$R^x$ is a C1–C8 alkyl group, preferably a C1–C3 alkyl group, more preferably a methyl group.

G is a substituted or unsubstituted aryl or heteraryl group. Preferably, G is Ring B or Ring C.

Ring B is

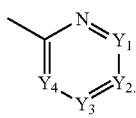

$Y_{1-4}$ are each independently selected from CH or nitrogen, provided that Ring B has no more than three nitrogen atoms and $Y_1$ and $Y_2$ are not both N, said Ring B being optionally substituted by $C_{1-4}$ aliphatic or haloaliphatic, $-OR^7$, $-SR^7$, $-C(O)R^7$, $-CO_2R^7$, $-SO_2R^7$, $-CN$, $-C(O)N(R^7)_2$, $-N(R^7)C(O)(C_{1-2}$ alkyl), or $-N(R^7)_2$.

Ring C is

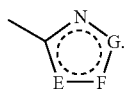

E—F—G is O—CH=CH, O—N=CH, CH—O—CH, CH=CH—O, S—CH=CH, or CH—S—CH, said Ring C being optionally substituted by $C_{1-4}$ aliphatic or haloaliphatic, $-OR^7$, $-SR^7$, $-C(O)R^7$, $-CO_2R^7$, $-SO_2R^7$, $-CN$, $-C(O)N(R^7)_2$, $-N(R^7)$ $C(O)C_{1-2}$alkyl), or $-N(R^7)_2$;

Each $R^7$ is independently selected from hydrogen or an optionally substituted $C_{1-3}$ aliphatic or $-N(R^7)_2$, taken together, is a nitrogen containing heterocyclyl.

Each $R^8$ and each q in the compound of Formula I is independently selected.

Each R is independently selected from hydrogen or an optionally substituted group selected from $C_{1-6}$ aliphatic, aryl, aralkyl, heteroaryl, or heteroaralkyl.

Another embodiment of the present invention is a method of treating cancer in a subject. The method comprises administering to the subject an effective amount of a compound of Formula I.

Yet another embodiment of the present invention is a compound of Formula II:

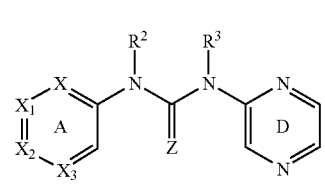

X, $X_{1-3}$, Ring A, R and $R^1$—$R^8$ in Formula II are as defined for Formula I, provided that $R^1$ is not tert-butyl. Ring D in Formula II is optionally substituted, as described above for Ring B in Formula I.

Yet another embodiment of the present invention is a compound represented by Structural Formula III:

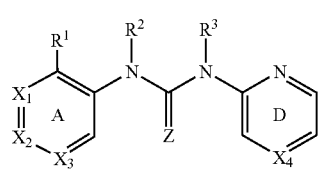

$R^1$ is $-V-T-NH_2$, $-T-NH_2$, $-V-T-NHR^x$ or $-T-NHR^x$ (preferably $-V-T-NH_2$, $-T-NH_2$).

$X_4$ is N or CH. In one preferred embodiment $X_4$ is CH. In another preferred embodiment, $X_4$ is N.

The remainder of the variables in Formula III are as described for Formula II above, provided, however, that Ring D is optionally substituted and is optionally fused to an optionally substituted six membered aromatic ring (preferably phenyl) or optionally substituted cyclohexyl ring. $R^x$ is a C1–C8 alkyl group, preferably a C1–C3 alkyl group, more preferably a methyl group. In preferred embodiment, i) $X_1$ is N and $X_2$ and $X_3$ are CH; $X_2$ is N and $X_1$ and $X_3$ are CH; $X_3$ is N and $X_1$ and $X_2$ are CH; $X_1$–$X_3$ are CH; ii) Ring A is optionally substituted at any substitutable carbon by $R^4$; and iii) the remainder of the variables in Formula III are as described above. It is more preferred that $X_1$–$X_3$ are CH; and Ring A optionally is substituted at any substitutable carbon by $R^4$.

Yet another embodiment of the present invention is a method of inhibiting Chk-1 in a subject in need of such treatment. The method comprises administering to the subject an effective amount of a compound of Formula III.

Yet another embodiment of the present invention is a method of treating cancer in a subject. The method comprises administering to the subject an effective amount of a compound of Formula III.

Yet another embodiment of the present invention is a pharmaceutical composition comprising a compound of Formula I, II or III and a pharmaceutically effective excipient, carrier or diluent. The pharmaceutical compositions can be used in therapy, e.g., to inhibit CHK-1 activity in a subject in need of such inhibition or to treat a subject with cancer.

Yet another embodiment of the present invention is the use of a compound of Formula I, II or III for the manufacture of a medicament for inhibiting Chk-1 in a subject in need of such inhibition or for treating a subject with cancer.

The compounds disclosed herein are effective inhibitors of Chk-1. They are therefore expected to be effective in treating subjects with cancer and enhancing the effectiveness of many current anti-cancer therapies, including radiation therapy and anti-cancer agents that exert their cytotoxic activity by damaging the genetic material of cancer cells and inhibiting cellular replication. In addition, the disclosed Chk-1 inhibitors, when used in combination with current anti-cancer therapies are expected to be effective against multidrug resistant cancers.

DETAILED DESCRIPTION OF THE INVENTION

The present invention is directed to novel methods of therapy utilizing the compounds of Formula I or III and to a novel compound of Formula II or III.

In a preferred embodiment, the compound of Formula I has one or more of the following features: (a) $R^2$ and $R^3$ are each hydrogen; (b) Z is oxygen; and, (c) G is Ring B; and the compound of Formula II and III has Feature (a) and/or Feature (b). More preferably, the compound of Formula I has Feature (a), Feature (b) and Feature (c); and the compound of Formula II and III has Feature (a) and (b). When the compound of Formula III has the features described in this paragraph, V is preferably —O—; T is preferably a $C_{2-5}$ alkylidene; and the remainder of the variables in Formula III are as described in the "Summary of the Invention".

Alternatively, the compound of Formulas I and II are as described in the previous paragraph, provided that X is C—T—NH$_2$, C—V—T—NH$_2$, C—T—NHR$^x$ or C—V—T—NHR$^x$. More preferably, V is —O— and T is a $C_{2-5}$ alkylidene chain.

In another preferred embodiment, the compound of Formula I and Formula II has Feature (d) wherein $R^1$ is V—T—$R^6$; V is —O—, T is a $C_{2-4}$ alkylidene chain, $R^6$ is —OR, —N(R)$_2$ or a 5–7 membered ring system wherein at least one of the ring atoms is a basic nitrogen, and each R is independently selected from hydrogen or a $C_{1-6}$ aliphatic. More preferably, $R^1$ is V—T—$R^6$ wherein V is —O—, T is a $C_{2-3}$ alkylidene chain, $R^6$ is —OR, —N(R)$_2$ or a 5–6 membered ring system wherein at least one of the ring atoms is a basic nitrogen, and each R is independently selected from hydrogen or a $C_{1-3}$ aliphatic. Even more preferably, $R^1$ is V—T—$R^6$ wherein V is —O—, T is an ethylene or propylene chain, $R^6$ is —OH, —N($C_{1-2}$ alkyl)$_2$, piperidin-1-yl, morpholin-4-yl, 4-substituted-piperazin-1-yl, pyrrol-1-yl, imidazol-1-yl, indol-1-yl, benzimidazol-1-yl, or 9H-carbazol-9-yl.

In a more preferred embodiment the compound of Formula I has Feature (d) and one or more of Features (a), (b) and (c); and the compound of Formula II has Feature (d) and one or more of Features (a) and (b). Even more preferably, the compound of Formula I has Features (a), (b), (c) and (d); and the compound of Formula II has Features (a), (b) and (d).

Alternatively, $R^1$ in the compounds defined herein is represented by —X—NH$_2$ or —X—NHR$^x$, wherein $R^x$ is as defined above and X is an inert linking group. As used herein, an inert linking group does not significantly diminish the activity of the compound towards Chk-1 and places the NH$_2$ or NHR$^x$ group at a specific distance from the aromatic group to which the inert linking group is bonded. Examples of inert linking group are provided by T or V—T, as defined above for Formula I. Typically, this specific distance corresponds to the length of an $C_{2-5}$ alkylidene or —O—$C_{2-5}$ alkylidene group.

Another embodiment of the present invention is one of the following compounds and the use thereof for inhibiting Chk-1 in a subject in need of such treatment and for the treatment of cancer, as described herein:

Compound 1

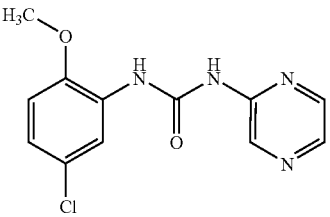

Compound 2

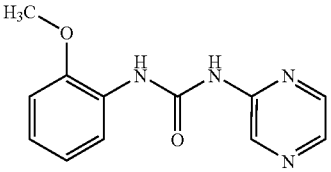

Compound 3

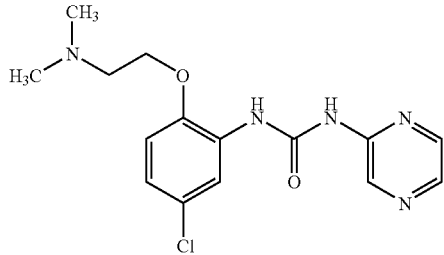

Compound 4

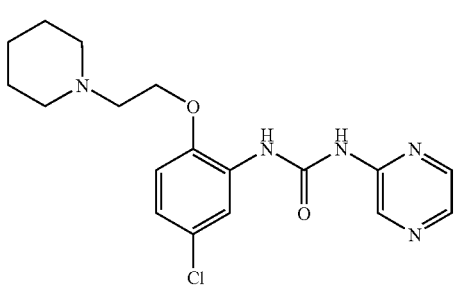

-continued
Compound 5
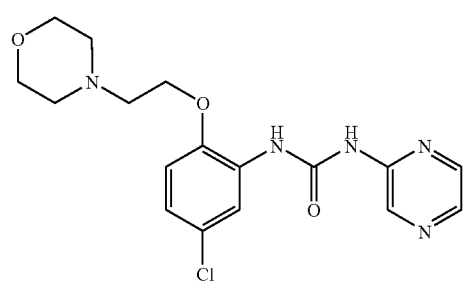
Compound 6
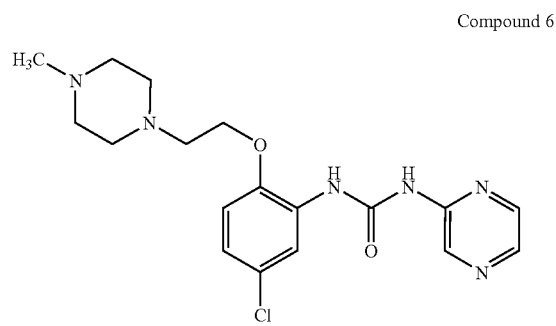
Compound 7
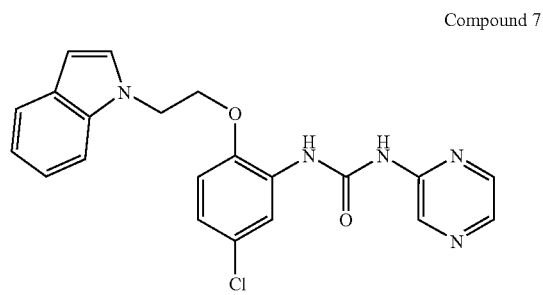
Compound 8
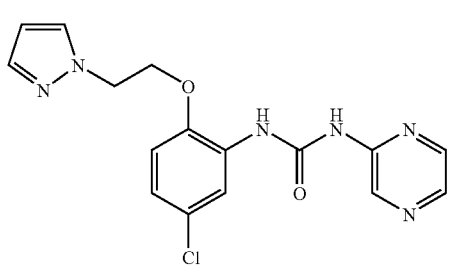
Compound 9
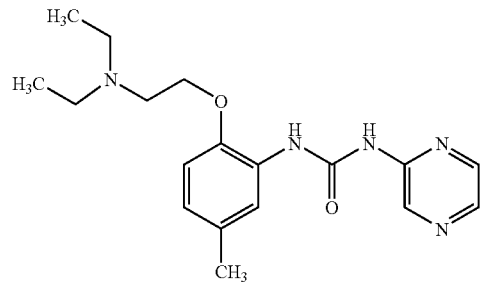
-continued
Compound 10
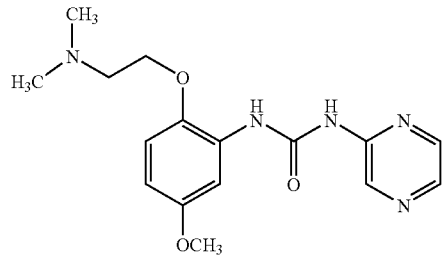
Compound 11
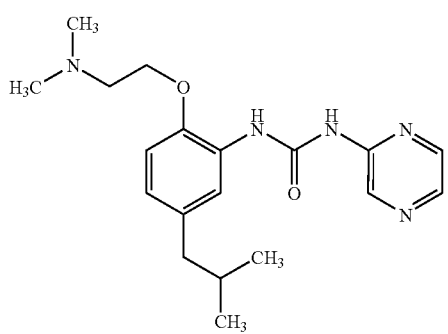
Compound 12
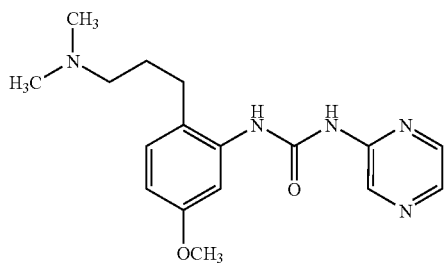
Compound 13
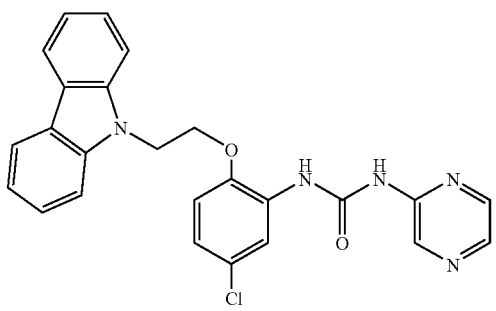
Compound 14
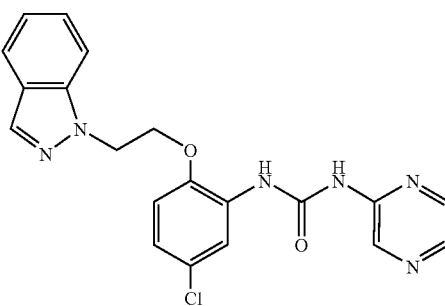

Compound 15

Compound 16

Compound 17

Compound 18

Compound 19

Compound 20

Compound 21

Compound 22

Compound 23

Compound 24

Compound 25

Compound 26

Compound 27

Compound 28
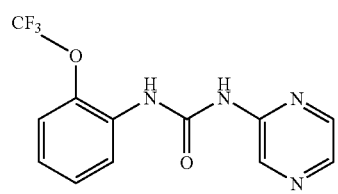
Compound 29
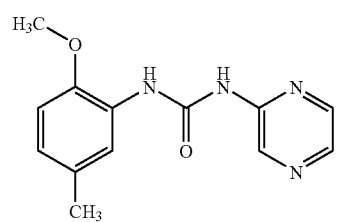
Compound 30
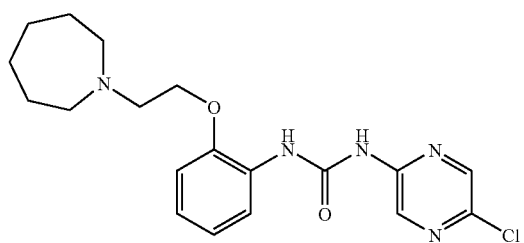
Compound 31
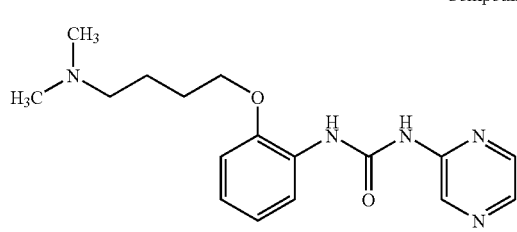
Compound 32
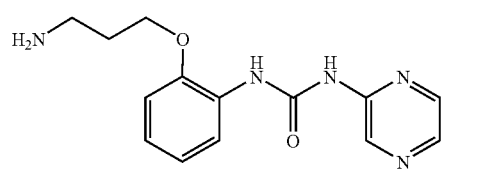
Compound 33
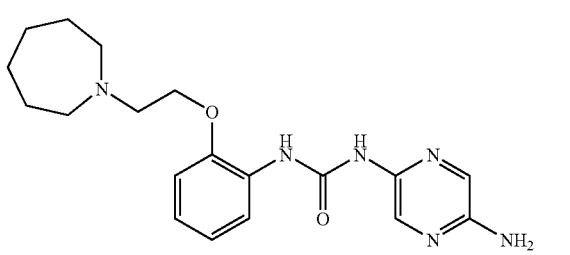
Compound 34
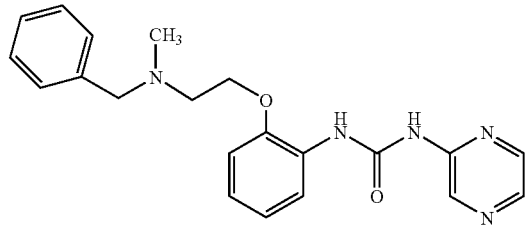
Compound 35
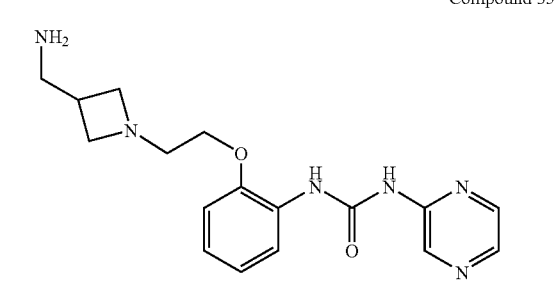
Compound 36
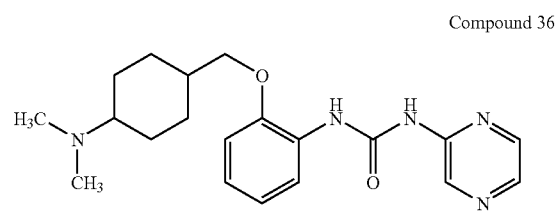
Compound 37
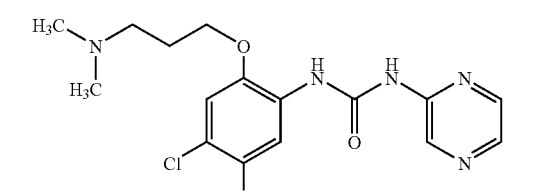
Compound 38
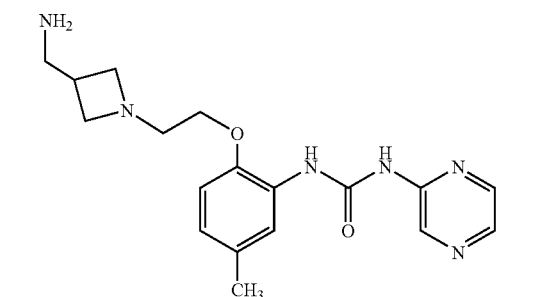
Compound 39
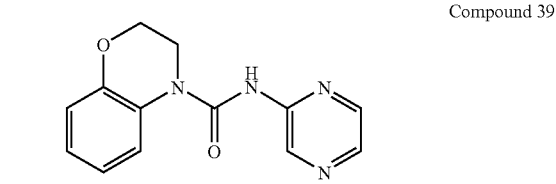

-continued
Compound 40
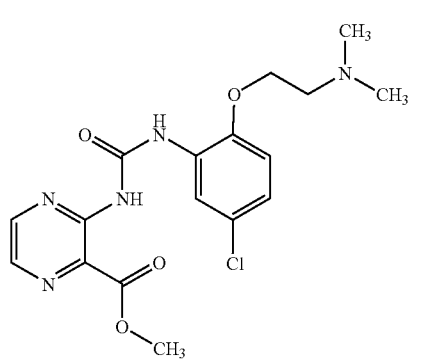
Compound 41
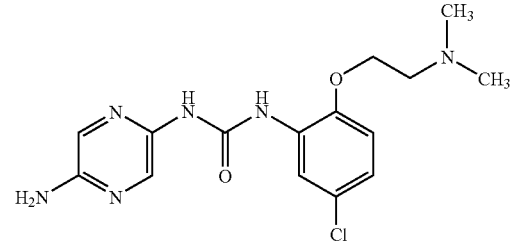
Compound 42
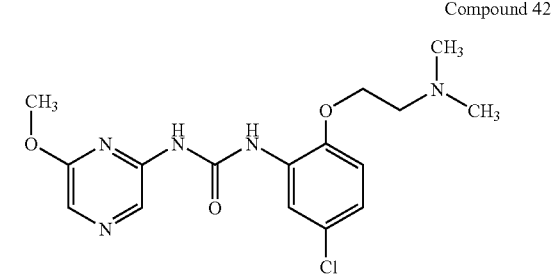
Compound 43
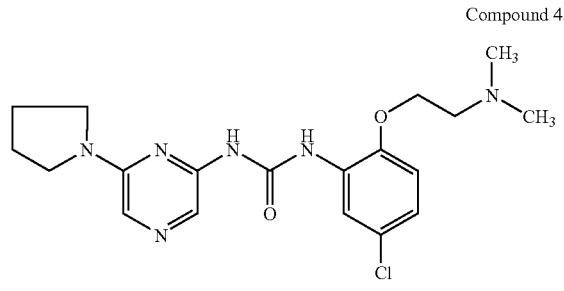
Compound 44
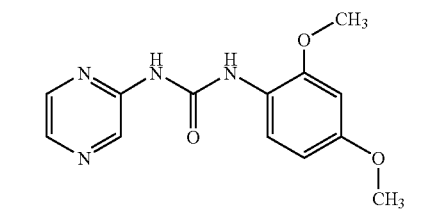
Compound 45
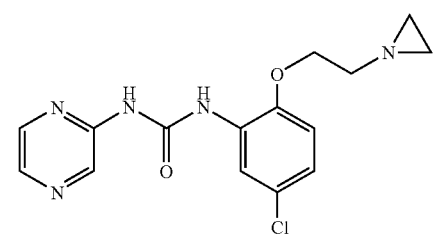
-continued
Compound 46
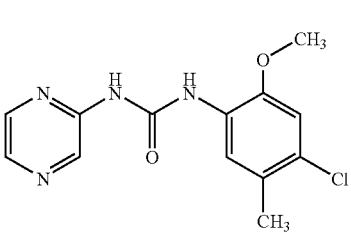
Compound 47
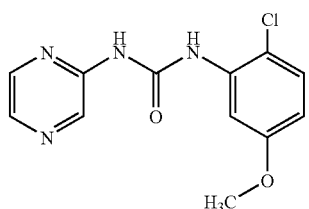
Compound 48
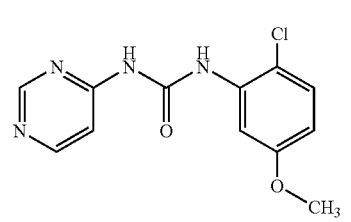
Compound 49
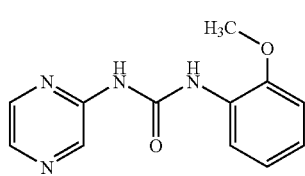
Compound 50
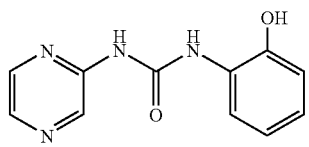
Compound 51
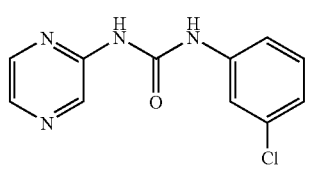
Compound 52
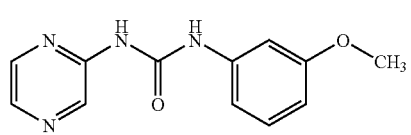
Compound 53
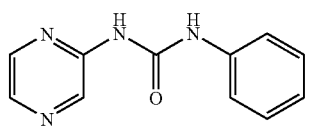
Compound 54
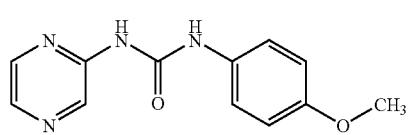

-continued
Compound 55
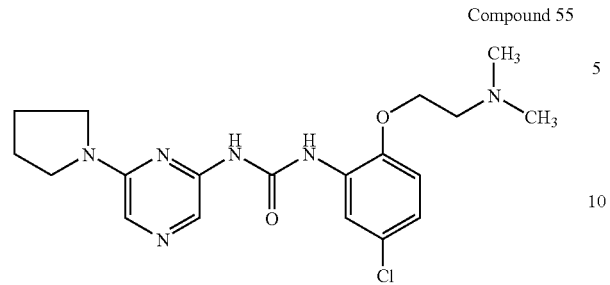
Compound 56
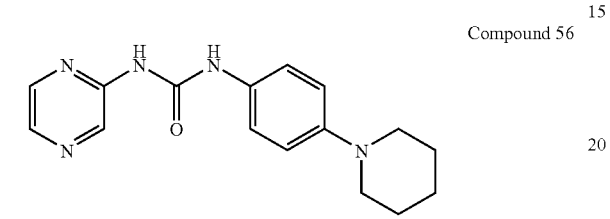
Compound 57
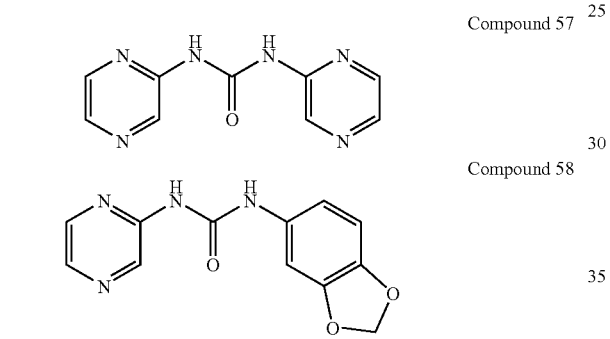
Compound 58
Compound 59
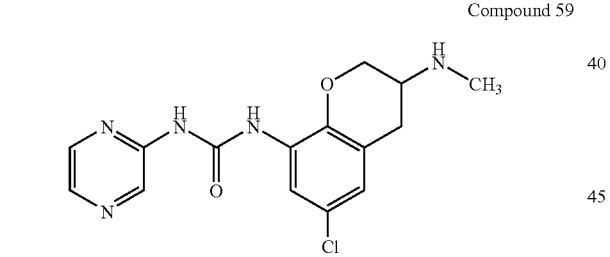
Compound 60
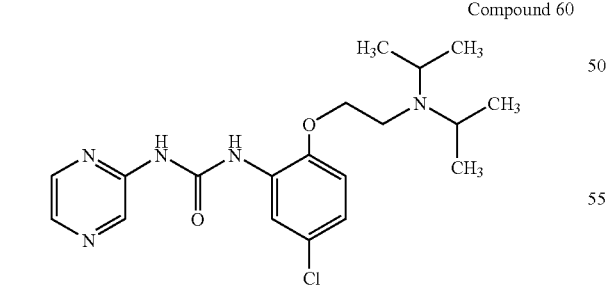
Compound 61
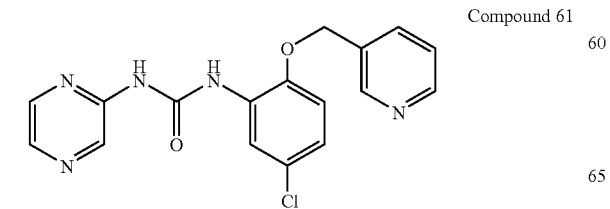
-continued
Compound 62
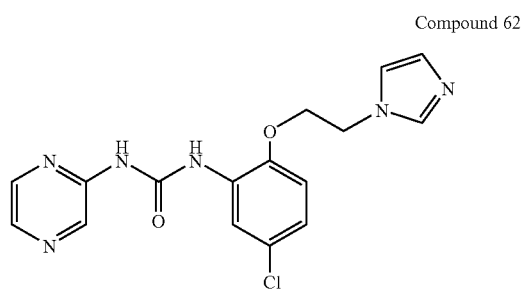
Compound 63
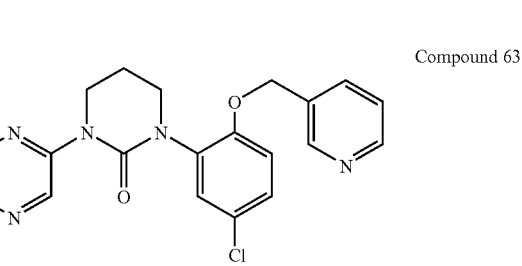
Compound 64
Compound 65
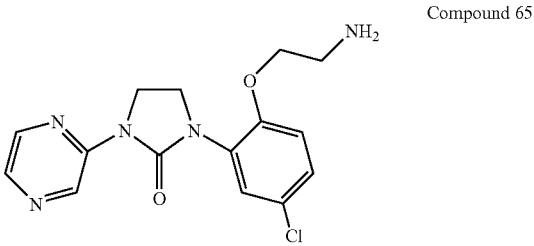
Compound 66
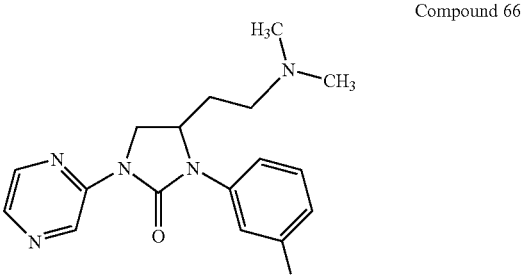
Compound 67
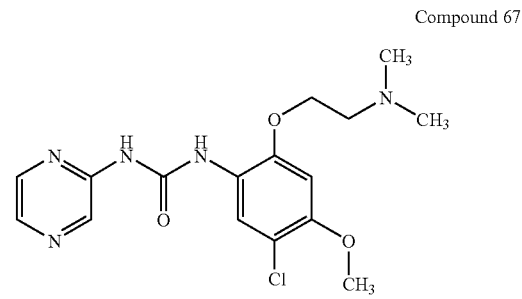

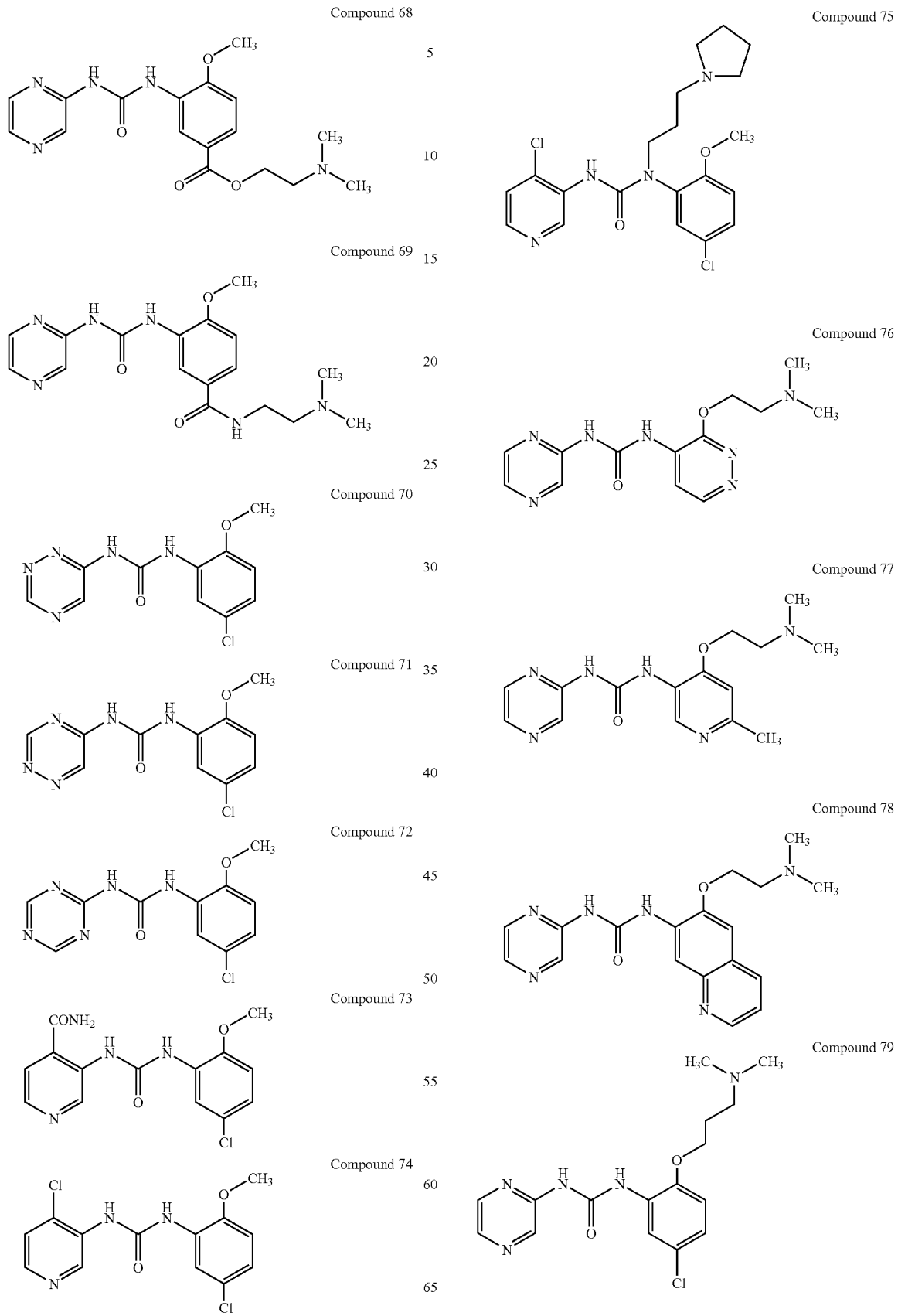

-continued
Compound 80
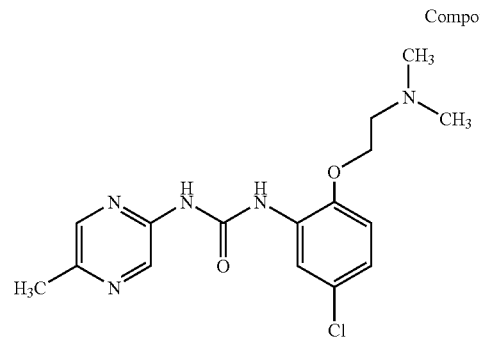
Compound 81
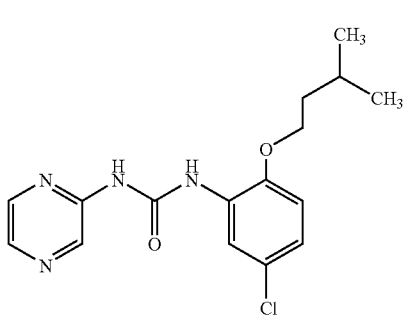
Compound 82
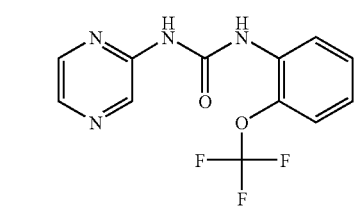
Compound 83
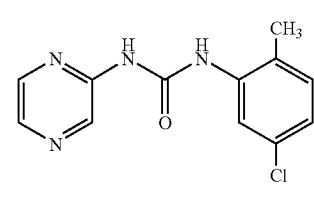
Compound 84
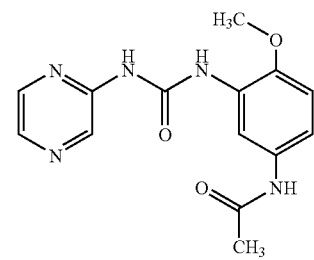
Compound 85
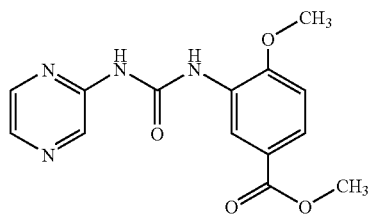
-continued
Compound 86
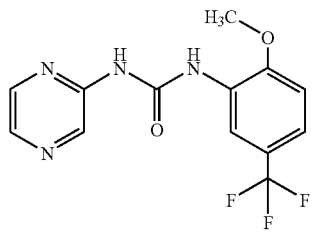
Compound 89
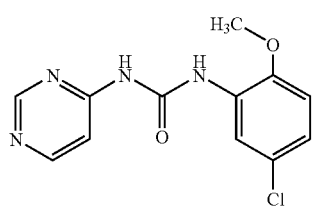
Compound 90
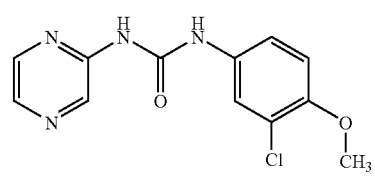
Compound 91
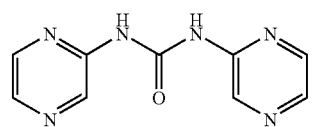
Compound 92
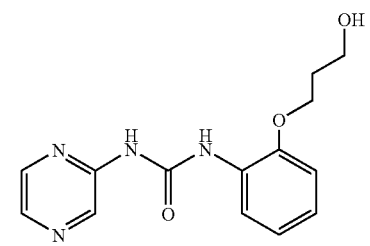
Compound 92
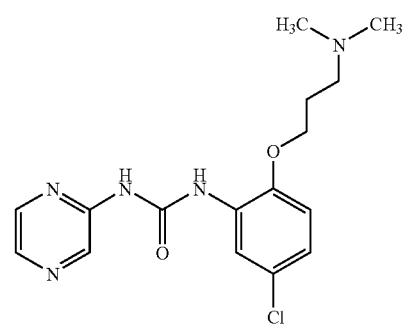

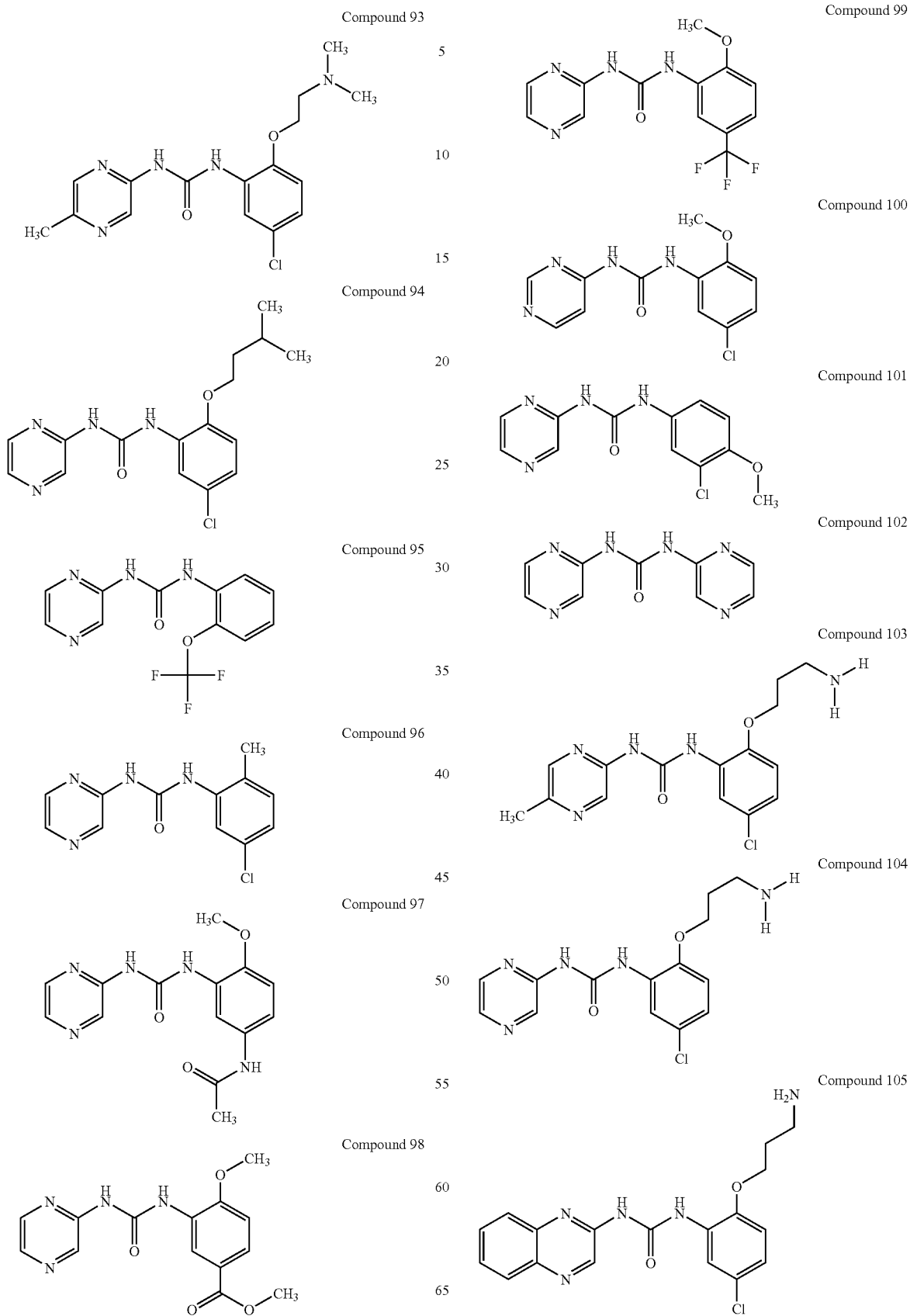

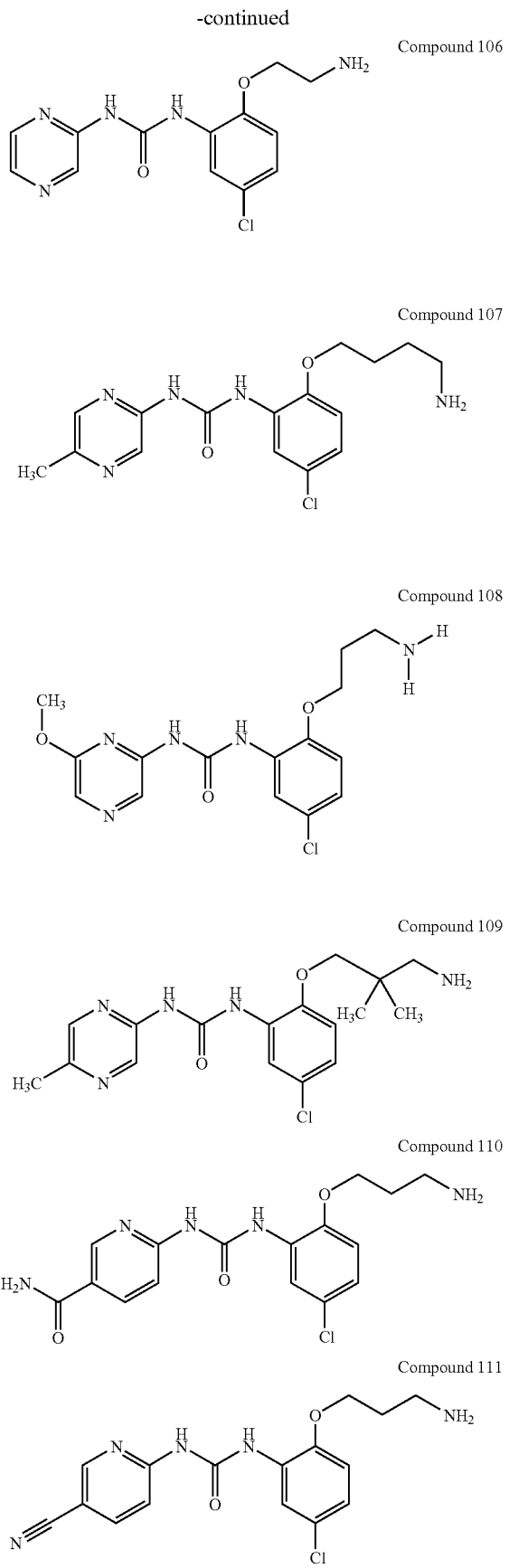
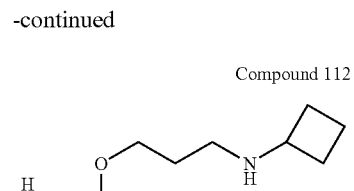

Another embodiment of the present invention is the use of a compound of Formula I for treating cancer or inhibiting Chk-1, as described herein, wherein Ring A has the value of the group at the corresponding position of any one of Compounds 1–112. Preferably, $R^2$ and $R^3$ are hydrogen and X is =O.

Another embodiment of the present invention is the use of a compound of Formula I for treating cancer or inhibiting Chk-1, as described herein, wherein G has the value of the group at the corresponding position of any one of Compounds 1–112. Preferably, $R^2$ and $R^3$ are hydrogen and X is =O.

Another embodiment of the present invention is a compound of Formula I wherein Ring A has the value of the group at the corresponding position of any one of Compounds 1–112. Preferably, $R^2$ and $R^3$ are hydrogen and X is =O.

Another embodiment of the present invention is a compound of Formula I wherein G has the value of the group at the corresponding position of any one of Compounds 1–112. Preferably, $R^2$ and $R^3$ are hydrogen and X is =O.

The term "aliphatic" as used herein means straight-chain, branched or cyclic hydrocarbons which are completely saturated or which contain one or more units of unsaturation, but which are not aromatic. When straight chained or branched, an aliphatic group is typically $C_{1-8}$, more typically $C_{1-6}$; when cyclic, an aliphatic group is typically $C_{3-10}$, more typically $C_{3-7}$. For example, suitable aliphatic groups include substituted or unsubstituted linear, branched or cyclic alkyl, alkenyl, alkynyl groups and hybrids thereof such as (cycloalkyl)alkyl, (cycloalkenyl)alkyl or (cycloalkyl)alkenyl. The terms "alkyl", "alkoxy", "hydroxyalkyl", "alkoxyalkyl", and "alkoxycarbonyl", used alone or as part of a larger moiety includes both straight and branched saturated chains containing one to eight carbon atoms. The terms "alkenyl" and alkynyl" used alone or as part of a larger moiety shall include both straight and branched chains containing two to eight carbon atoms and one or more double or triple bonds, respectively. The term "cycloaliphatic" used alone or as part of a larger moiety shall include cyclic $C_3$–$C_{10}$ hydrocarbons which are completely saturated or which contain one or more units of unsaturation, but which are not aromatic. A "cycloalkyl" is an cyclic aliphatic group that is completely saturated.

The terms "haloaliphatic", "haloalkyl", "haloalkenyl" and "haloalkoxy" means aliphatic, alkyl, alkenyl or alkoxy, as the case may be, substituted with one or more halogen atoms. The term "halogen" means F, Cl, Br or I.

The term "heteroatom" means nitrogen, oxygen, or sulfur and includes any oxidized form of nitrogen and sulfur, and the quaternized form of any basic nitrogen. Also the term "nitrogen" includes a substitutable nitrogen of a heterocyclic ring. As an example, in a saturated or partially unsaturated ring having 0–3 heteroatoms selected from oxygen, sulfur or nitrogen, the nitrogen may be N (as in 3,4-dihydro-2H-pyrrolyl), NH (as in pyrrolidinyl) or NR$^+$ (as in N-substituted pyrrolidinyl).

The term "aryl" used alone or as part of a larger moiety as in "aralkyl", "aralkoxy", or "aryloxyalkyl", refers to aromatic ring groups, typically having five to fourteen members, such as phenyl, benzyl, phenethyl, 1-napthyl, 2-naphthyl, 1-anthracyl and 2-anthracyl. The term "aryl" also refers to rings that are optionally substituted. The term "aryl" may be used interchangeably with the term "aryl ring". "Aryl" also includes fused polycyclic aromatic ring systems in which an aromatic ring is fused to one or more rings. Examples include 1-naphthyl, 2-naphthyl, 1-anthracyl and 2-anthracyl. Also included within the scope of the term "aryl", as it is used herein, is a group in which an aromatic ring is fused to one or more non-aromatic rings, such as in an indanyl, phenantriidinyl, or tetrahydronaphthyl, where the radical or point of attachment is on the aromatic ring.

The term "heterocycle", "heterocyclyl", or "heterocyclic", used alone or as part of a larger moiety as in "heterocyclylalkyl", refers to non-aromatic ring systems typically having five to fourteen members, preferably five to ten, in which one or more ring carbons, preferably one to four, are each replaced by a heteroatom such as N, O, or S. Examples of heterocyclic rings include 3-1H-benzimidazol-2-one, 3-tetrahydrofuranyl, 2-tetrahydropyranyl, 3-tetrahydropyranyl, 4-tetrahydropyranyl, [1,3]-dioxalanyl, [1,3]-dithiolanyl, [1,3]-dioxanyl, 2-tetrahydrothiophenyl, 3-tetrahydrothiophenyl, 2-morpholinyl, 3-morpholinyl, 4-morpholinyl, 2-thiomorpholinyl, 3-thiomorpholinyl, 4-thiomorpholinyl, 1-pyrrolidinyl, 2-pyrrolidinyl, 3-pyrorolidinyl, 1-piperazinyl, 2-piperazinyl, 1-piperidinyl, 2-piperidinyl, 3-piperidinyl, 4-piperidinyl, 4-thiazolidinyl, diazolonyl, N-substituted diazolonyl, 1-pthalimidinyl, benzoxanyl, benzopyrrolidinyl, benzopiperidinyl, benzoxolanyl, benzothiolanyl, and benzothianyl. Also included within the scope of the term "heterocyclyl" or "heterocyclic", as it is used herein, is a group in which a non-aromatic heteroatom-containing ring is fused to one or more aromatic or non-aromatic rings, such as in an indolinyl, chromanyl, phenantrhidinyl, or tetrahydroquinolinyl, where the radical or point of attachment is on the non-aromatic heteroatom-containing ring. The term "heterocycle", "heterocyclyl", or "heterocyclic" whether saturated or partially unsaturated, also refers to rings that are optionally substituted.

The term "heteroaryl", used alone or as part of a larger moiety as in "heteroaralkyl" or "heteroarylalkoxy", refers to heteroaromatic ring groups having five to fourteen members. Examples of heteroaryl rings include 2-furanyl, 3-furanyl, N-imidazolyl, 2-imidazolyl, 4-imidazolyl, 5-imidazolyl, 3-isoxazolyl, 4-isoxazolyl, 5-isoxazolyl, 2-oxadiazolyl, 5-oxadiazolyl, 2-oxazolyl, 4-oxazolyl, 5-oxazolyl, 1-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, 3-pyridazinyl, 2-thiazolyl, 4-thiazolyl, 5-thiazolyl, 2-triazolyl, 5-triazolyl, 2-thienyl, 3-thienyl, carbazolyl, benzimidazolyl, benzothienyl, benzofuranyl, indolyl, quinolinyl, benzotriazolyl, benzothiazolyl, benzooxazolyl, benzimidazolyl, isoquinolinyl, indolyl, isoindolyl, acridinyl, or benzoisazolyl. Also included within the scope of the term "heteroaryl", as it is used herein, is a group in which a heteroatomic ring is fused to one or more aromatic or nonaromatic rings where the radical or point of attachment is on the heteroaromatic ring. Examples include tetrahydroquinolinyl, tetrahydroisoquinolinyl, and pyrido [3, 4-d] pyrimidinyl. The term "heteroaryl" also refers to rings that are optionally substituted. The term "heteroaryl" may be interchangeably with the term "heteroaryl ring" or the term "heteroaromatic".

An "aralkyl", "heteroaralkyl" and "heterocyclylalkyl" is an alkyl group, typically a $C_{1-8}$ alkyl group, substituted with an aryl group (preferably a phenyl group), heteroaryl and heterocyclyl, respectively.

An "alkylidene chain" is a polymethylene group, i.e., $-(CH_2)_n-$, wherein n is a positive integer. Preferably, n is an integer from 1 to 6, more preferably from 2 to 4 and more preferably from 2 to 3. A "substituted alkylidine chain" is an alkylidine in which one or more methylene hydrogen atoms are replaced with a substituent. Suitable substituents are as described below for a substituted aliphatic group.

An alkylidine chain can be optionally interrupted by a functional group. An alkylidine chain is interrupted by a functional group when one of the methylenes is replaced with the functional group. Examples of suitable "interrupting functional groups" include $-O-$, $-S-$, $-N(R^5)-$, $-S(O)-$, $-SO_2-$, $-C(O)-$, $-OC(O)-$, $-N(R^5)C(O)-$, $-C(O)N(R^5)-$, $-SO_2N(R^5)-$, and $-N(R^5)SO_2-$. $R^5$ is as described above. Examples of alkylidene chains which have been "interrupted" with $-O-$ include $-O-$, $-O(CH_2)-$, $-O(CH_2)_2-$, $-O(CH_2)_3-$, $-O(CH_2)_4-$, $-O(CH_2)_5-$, $-CH_2O-$, $-CH_2O(CH_2)-$, $-CH_2O(CH_2)_2-$, $-CH_2O(CH_2)_3-$, $-CH_2O(CH_2)_4-$, $-(CH_2)_2O-$, $-(CH_2)_2O(CH_2)-$, $-(CH_2)_2O(CH_2)_2-$, $-(CH_2)_2O(CH_2)_3-$, $-(CH_2)_3O-$, $-(CH_2)_3O(CH_2)-$, $-(CH_2)_3O(CH_2)_2-$, $-(CH_2)_4O-$, $-(CH_2)_4O(CH_2)-$ and $-(CH_2)_5O-$. Other examples of alkylidene chains which have been "interrupted" with functional groups include $-M(CH_2)-$, $-M(CH_2)_2-$, $-M(CH_2)_3-$, $-M(CH_2)_4-$, $-M(CH_2)_5-$, $-CH_2M-$, $-CH_2M(CH_2)-$, $-CH_2M(CH_2)_2-$, $-CH_2M(CH_2)_3-$, $-CH_2M(CH_2)_4-$, $-(CH_2)_2M-$, $-(CH_2)_2M(CH_2)-$, $-(CH_2)_2M(CH_2)_2-$, $-(CH_2)_2M(CH_2)_3-$, $-(CH_2)_3M-$, $-(CH_2)_3M(CH_2)-$ $-(CH_2-$ $-_{(CH2)}4M(CH_2)-$ and $-(CH_2)_5O-$, wherein M is one of the "interrupting" functional groups listed above.

An aryl (including aralkyl, aralkoxy, aryloxyalkyl and the like) or heteroaryl (including heteroaralkyl and heteroarylalkoxy and the like) group may contain one or more substituents. Examples of suitable substituents on an unsaturated carbon atom of an aryl, heteroaryl, aralkyl, or heteroaralkyl group include a halogen $-R^o$, $-OR^o$, $-SR^o$, 1,2-methylene-dioxy, 1,2-ethylenedioxy, protected OH (such as acyloxy), phenyl (Ph), substituted Ph, $-O(Ph)$, substituted $-O(Ph)$, $-CH_2(Ph)$, substituted $-CH_2(Ph)$, $-CH_2CH_2(Ph)$, substituted $-CH_2CH_2(Ph)$, $-NO_2$, $-CN$, $-N(R')_2$, $-NR'CO_2R^o$, $NR'C(O)R^o$, $-NR'NR'C(O)R^o$, $-N(R')C(O)N(R')_2$, $-NR'NR'C(O)N(R')_2$, $-NR'NR'CO_2R^o$, $-C(O)C(O)R^o$, $-C(O)CH_2C(O)R^o$, $-CO_2R^o$, $-C(O)R^o$, $-C(O)N(R^o)_2$, $-OC(O)N(R^o)_2$, $-S(O)_2R^o$, $-SO_2N(R')_2$, $-S(O)R^o$, $-NR'SO_2N(R')_2$, $-NR'SO_2R^o$, $-C(=S)N(R')_2$, $-(CH_2)_yNR')_2$, $-C(=NH)-N(R')_2$, $-(CH_2)_yNHC(O)R^o$, $-(CH_2)_yNHC(O)CH(V-R^o)(R^o)$. R' is $R^o$, $-CO_2R^o$, $-SO_2R^o$ or $-C(O)R^o$ and preferably hydrogen, $C_{1-6}$ aliphatic, $CO_2R^o$, $SO_2R^o$ or $C(O)R^o$. $R^o$ is hydrogen or substituted or unsubstituted aliphatic, aryl, aralkyl, heterocyclyl, heterocyclylalkyl or heteroaryl and preferably hydrogen, $C_{1-6}$ alkyl, phenyl (Ph), —CH$_2$ (Ph), aralkyl, heterocyclyl, heterocyclylalkyl or heteroaryl; y is 0–6; and V is a linker group. Examples of substituents on the aliphatic group or the phenyl ring of R$^o$ include amino, alkylamino, dialkylamino, aminocarbonyl, halogen, alkyl, aminoalkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl. Preferred substituents for Ring A are substituents represented by R$^4$; and preferred substituents for Rings B and C are C$_{1-4}$ aliphatic or haloaliphatic, —OR$^7$, —SR$^7$, —C(O)R$^7$, —CO$_2$R$^7$, —SO$_2$R$^7$, —CN, —C(O)N(R$^7$)$_2$, —N(R$^7$)C(O)(C$_{1-2}$ alkyl), or —N(R$^7$)$_2$, wherein R$^7$ is as defined above. Certain particularly preferred substitutents for Ring B are —CN, —COOR$^7$ and —CON(R$^7$)$_2$ at the position para to the carbon bonded to the urea nitrogen. These substituents are even more preferred when Ring B is pyridine.

An alphatic group or a heterocycle may contain one or more substituents. Examples of suitable substituents on the saturated carbon of an aliphatic group of a heterocycle include those listed above for the unsaturated carbon of an aryl or heteroaryl group and the following: =O, =S, =NNHR*, =NN(R*)$_2$, =NNHC(O)R*, =NNHCO$_2$ (alkyl), =NNHSO$_2$ (alkyl), or =NR*. Each R* is independently selected from hydrogen, an unsubstituted aliphatic group or a substituted aliphatic group. Examples of substituents on the aliphatic group represented by R* include amino, alkylamino, dialkylamino, aminocarbonyl, halogen, alkyl, alkylaminocarbonyl, dialkylaminocarbonyl, alkylaminocarbonyloxy, dialkylaminocarbonyloxy, alkoxy, nitro, cyano, carboxy, alkoxycarbonyl, alkylcarbonyl, hydroxy, haloalkoxy, or haloalkyl.

Suitable substitutents on the nitrogen of a heterocycle include —R$^+$, —N(R$^+$)$_2$, —C(O)R$^+$, —CO$_2$ R$^+$, —C(O)C(O)R$^+$, —C(O)CH$_2$C(O)R$^+$, —SO$_2$ R$^+$, —SO$_2$ N(R$^+$)$_2$, —C(=S)N(R$^+$)$_2$, —C(=NH)—N(R$^+$)$_2$, and —NR$^+$SO$_2$ R$^+$; wherein R$^{++}$ is hydrogen, an aliphatic group, a substituted aliphatic group, phenyl (Ph), substituted Ph, —O(Ph), substituted —O(Ph), CH$_2$(Ph), or an unsubstituted heteroaryl or heterocyclic ring. Examples of substituents on the aliphatic group or the phenyl ring represented by R$^+$ include amino, alkylamino, dialkylamino, aminocarbonyl, halogen, alkyl, alkylaminocarbonyl, dialkylaminocarbonyloxy, alkoxy, nitro, cyano, carboxy, alkoxycarbonyl, alkylcarbonyl, hydroxy, haloalkoxy, or haloalkyl.

As noted above, Ring A of Formula III is optionally substituted with one or more groups R$^4$ and Ring D of Formula III is optionally substituted with C$_{1-4}$ aliphatic, C$_{1-4}$ haloaliphatic, —OR$^7$, —SR$^7$, —C(O)R$^7$, —CO$_2$R$^7$, —SO$_2$R$^7$, —CN, —C(O)N(R$^7$)$_2$, —N(R$^7$)C(O)(C$_{1-2}$ alkyl) or —N(R$^7$)$_2$ and is optionally fused to a six membered aromatic ring (preferably phenyl) or cyclohexyl ring. R$^4$ and R$^7$ are as described above and the fused six membered or cyclohexyl ring are optionally substituted. Preferably, at least one R$^4$ is para to the carbon bonded with R$^1$ and Ring D, is optionally substituted meta and/or para to the carbon bonded with the urea nitrogen. More preferably Ring A is monosubstitutedpara to the carbon bonded with the R$^1$ and Ring D is optionally monosubstituted meta or para to the carbon bonded with the urea nitrogen. Preferred values for R$^4$ are —F, —Cl, —Br, —I, —COOR$^a$, —NHCOR$^a$, —CF$_3$, —CH$_3$, —CH$_2$CH$_3$, —CH(CH$_3$)$_2$, —N(R$^a$)$_2$, —CH$_2$N(R$^a$)$_2$, —CH$_2$CH$_2$N(R$^a$)$_2$, piperidinyl, morpholinyl and pyrrolidinyl, wherein R$^a$ is —CH$_3$, —CH$_2$CH$_3$, —CH$_2$CH$_2$NH$_2$, —CH$_2$CH$_2$NH(CH$_3$), —CH$_2$CH$_2$N(CH$_3$)$_2$, —CH$_2$CH$_2$(N-morpholinyl), —CH$_2$CH$_2$ (N-piperidinyl) or —CH$_2$CH$_2$(N-pyrrolidinyl). Preferred substituents for Ring D of Formula III include methyl, —OCH$_3$, —NH$_2$, phenyl fused to Ring D or cyclohexyl fused to Ring D. Suitable substituents for a cyclohexyl or six membered aromatic ring fused to Ring D are as described above for aliphatic and aryl ring substituents. Preferred substituents for these fused rings include methoxy, methyl, halogen, nitro and cyano. Other preferred substituents for Ring D include —CO$_2$R$^7$, —CN or —C(O)N(R$^7$)$_2$ at the position para to the carbon atom bonded to the urea nitrogen.

Additionally, pharmaceutically acceptable salts of the compounds of Formula I, II and III are included in the present invention. For example, an acid salt of a compound containing an amine or other basic group can be obtained, by reacting the compound with a suitable organic or inorganic acid, such as hydrogen chloride, hydrogen bromide, acetic acid, perchloric acid and the like. Compounds with a quaternary ammonium group also contain a counteranion such as chloride, bromide, iodide, acetate, perchlorate and the like. Other examples of such salts include hydrochlorides, hydrobromides, sulfates, methanesulfonates, nitrates, maleates, acetates, citrates, fumarates, tartrates [e.g. (+)-tartrates, (−)-tartrates or mixtures thereof including racemic mixtures], succinates, benzoates and salts with amino acids such as glutamic acid.

Salts of compounds containing a carboxylic acid or other acidic functional group can be prepared by reacting with a suitable base. Such a pharmaceutically acceptable salt may be made with a base which affords a pharmaceutically acceptable cation, which includes alkali metal salts (especially sodium and potassium), alkaline earth metal salts (especially calcium and magnesium), aluminum salts and ammonium salts, as well as salts made from physiologically acceptable organic bases such as trimethylamine, triethylamine, morpholine, pyridine, piperidine, picoline, dicyclohexylamine, N,N'-dibenzylethylenediamine, 2-hydroxyethylamine, bis-(2-hydroxyethyl)amine, tri-(2-hydroxyethyl)amine, procaine, dibenzylpiperidine, N-benzyl-β-phenethylamine, dehydroabietylamine, N,N'-bisdehydroabietylamine, glucamine, N-methylglucamine, collidine, quinine, quinoline, and basic amino acid such as lysine and arginine.

The disclosed Chk-1 inhibitors are advantageously administered to inhibit Chk-1 in a subject in whom a beneficial therapeutic or prophylactic effect can be achieved by inhibiting Chk-1, i.e., a subject in need of Chk-1 inhibition. A "subject" is a mammal, preferably a human, but can also be an animal in need of veterinary treatment, e.g., companion animals (e.g., dogs, cats, and the like), farm animals (e.g., cows, sheep, pigs, horses, and the like) and laboratory animals (e.g., rats, mice, guinea pigs, and the like).

Chk-1 inhibition can be used to achieve a beneficial therapeutic or prophylactic effect, for example, in subjects with cancer. Cancers which can be treated with Chk-1 inhibitors include cancers or cell types (e.g., solid tumors such as colon, breast, lung, ovarian, pancreatic or non-solid tumors such as non-Hodgkins lymphomas and leukemias) in which p53 or the p53 pathway has been inactivated or abrogated. Chk-1 inhibitors are particularly useful in the treatment of cancers or cell types in which Chk-1 protein or activity is up regulated (e.g., retinoblastomas such as Rb negative or inactivated cells or where the ARF$^{p14/p19}$ locus has been inactivated or misregulated. Use of Chk-1 inhibitors as drugs for the treatment of cancer is particularly advantageous and can enhance the effectiveness of the treatment when: 1) combined with radiation therapy or with an anti-cancer drugs which act by causing damage to the genetic material of cells (referred to herein as "DNA damaging anti-cancer drugs"); 2) combined with agents which are otherwise cytotoxic to cancer cells during cell division; 3) combined with agents which are proteasome inhibitors; 4) combined with agents which inhibit NF-κB (e.g., IKK inhibitors); or 5) used with combinations of cancer drugs with which are not cytotoxic when administered alone, yet in combination produce a toxic effect. Examples of DNA damaging anti-cancer drugs include Topoisomerase I inhibitors (e.g., irinotecan, camptothecin and analogs or metabolites thereof and doxorubicin); Topoisomerase II inhibitors (e.g., etoposide and daunorubicin); alkylating agents (e.g., methotrexate or cyclophosphamide); DNA intercalators (e.g., cisplatin and carboplatin); DNA intercalators and free radical generators such as bleomycin; and nucleoside mimietics (e.g., 5-fluorouracil gemcitabine and hydroxyurea). Agents which disrupt cell replication include: taxol, taxol analogs vinblastin and vinblastin analogs); antibodies such as Trastuzumab (Herceptin) which bind to proteins overexpressed in cancers and thereby downregulate cell replication; and inhibitors such as STI-571 (e.g., Gleeveec) of proteins or enzymes known to be upregulated, over-expressed or activated in cancers, the inhibition of which downregulates cell replication.

The disclosed Chk-1 inhibitors are also effective when used in combination with DNA-damaging anti-cancer drugs and/or radiation therapy to treat subjects with multi-drug resistant cancers. A cancer is resistant to a drug when it resumes a normal rate of tumor growth while undergoing treatment with the drug after the tumor had initially responded to the drug. A tumor "responds to a drug" when it exhibits a decrease in tumor mass or a decrease in the rate of tumor growth. The term "multi-drug resistant cancer" refers to cancer that is resistant to two or more drugs, typically five or more.

As such, an "effective amount" of the disclosed Chk-1 inhibitors is the quantity which inhibits Chk-1 when administered to a subject or which, when administered to a subject with cancer, slows tumor growth, ameliorates the symptoms of the disease and/or increases longevity. When used in combination with radiation therapy, with a DNA-damaging drug or other anti-cancer drug, an effective amount of the Chk-1 inhibitor is the quantity in which a greater response is achieved when the Chk-1 inhibitor is co-administered with the DNA damaging anti-cancer drug and/or radiation therapy compared with when the DNA damaging anti-cancer drug and/or radiation therapy is administered alone. When used as a combination therapy, an "effective amount" of the DNA damaging drug and/or an "effective" radiation dose are administered to the subject, which is a quantity in which anti-cancer effects are normally achieved. The disclosed Chk-1 inhibitors and the DNA damaging anti-cancer drug can be co-administered to the subject as part of the same pharmaceutical composition or, alternatively, as separate pharmaceutical compositions. When administered as separate pharmaceutical compositions, the disclosed Chk-1 inhibitors and the DNA-damaging anti-cancer drug (and/or radiation therapy) can be administered simultaneously or at different times, provided that the enhancing effect of the Chk-1 inhibitor is retained.

The amount of Chk-1 inhibitor, DNA damaging anti-cancer drug and radiation dose administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used anti-cancer drugs and radiation therapy are well known to the skilled person. Effective amounts of the disclosed Chk-1 inhibitors typically range between about 1 mg/mm$^2$ per day and about 10 grams/mm$^2$ per day, and preferably between 10 mg/mm$^2$ per day and about 5 grams/mm$_2$.

The Chk-1 inhibitors described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The Chk-1 inhibitor will be present in such pharmaceutical compositions in amounts sufficient to provide the desired dosage amount in the range described herein. Techniques for formulation and administration of the compounds of the instant invention can be found in *Remington: the Science and Practice of Pharmacy,* 19$^{th}$ edition, Mack Publishing Co., Easton, Pa. (1995).

For oral administration, the Chk-1 inhibitor or salts thereof can be combined with a suitable solid or liquid carrier or diluent to form capsules, tablets, pills, powders, syrups, solutions, suspensions and the like.

The tablets, pills, capsules, and the like contain from about 1 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parental administration the disclosed Chk-1 inhibitor, or salts thereof can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

Preferably disclosed Chk-1 inhibitors or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient (viz., a compound of Structural Formula I, II or III or salts thereof) in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

A synthesis for the preparation of the Chk-1 inhibitors disclosed herein is shown below in the Synthetic Scheme. Specific conditions for carrying out these reactions are provided in Examples 1–28.

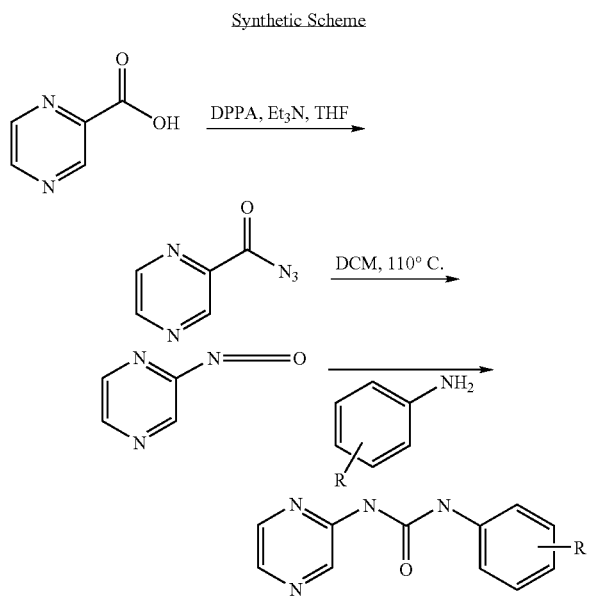

The invention is illustrated by the following examples, which are not intended to be limiting in any way.

EXEMPLIFICATION

Example 1

1-[5-Chloro-2-(3-dimethylamino-propoxy)-phenyl]-3-pyrazin-2-yl-urea

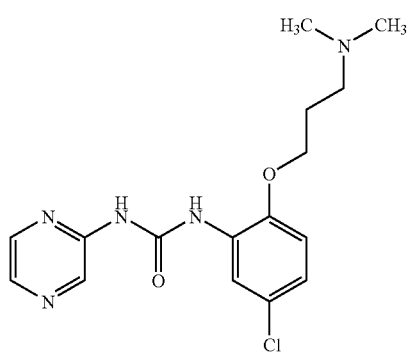

The title compound was prepared from the appropriate reagents, using a procedure similar to that described in Example 2. 1H NMR (400 MHz, DMSO-d6) δ10.6 (s, 1H, broad); 10.39 (s, 1H); 8.71 (s, 1H); 8.31 (d, 1H, J=2.2); 8.30 (dd, 1H, J=2.7, 1.6); 8.27 (d, 1H, J=2.7); 7.06 (d, 1H, J=8.6); 7.02 (dd, 1H, J=8.6, 2.2); 4.10(t, 2H, J=6.2); 2.40 (t, 2H, J=7.1); 2.19 (s, 6H); 1.96 (td, 2H, J=7.1, 6.2). LCMS: method A, RT=2.55 min, [MH$^+$=350, MNa$^+$=373].

Example 2

1-[5-Chloro-2-(2-dimethylamino-ethoxy)-phenyl]-3-pyrazin-2-yl-urea

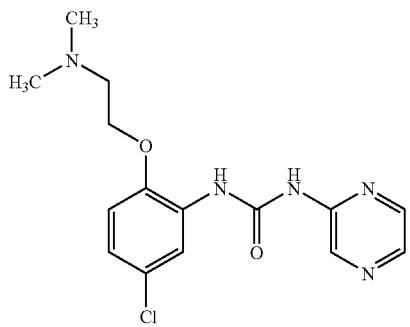

Step 1

5-Chloro-2-(2-dimethylamino-ethoxy)-phenylamine

To a suspension of 2-Amino-4-chloro-phenol (1.43 g, 10 mmoles, 1 eq) and potassium carbonate (6.9 g, 50 mmoles, 5 eq) in acetone (25 ml) was added in one portion (2-Chloro-ethyl)-dimethyl-amine hydrochloride (2.16 g, 15 mmoles, 1.5 eq). The reaction mixture was refluxed under Nitrogen for 6 hours at which time the suspension was filtered and the solid washed with acetone. The combined filtrate was concentrated under vacuum and purified by flash chromatography (EtOAc/MeOH/NEt$_3$: 87/9/3) to afford a beige solid (1.6 g, yield=72%).

1H NMR (400 MHz, DMSO-d6) δ 6.78 (d, 1H, J=8.6); 6.63 (d, 1H, J=2.5); 6.47 (dd, 1H, J=8.6, 2.5); 5.03 (s, 2H, broad); 3.88 (t, 2H, J=5.8); 2.60 (t, 2H, J=5.8); 2.21 (s, 6H). LCMS: method A, RT=0.5 min, [MH$^+$=215].

Step 2

Pyrazine-2-carbonyl azide

To a solution of Pyrazine-2-carboxylic acid (295 mg, 2.1 mmol, 1 eq) and triethylamine (765 ul, 5.4 mmol, 2.6 eq) in THF (6 ml) at 0° C. was added dropwise diphenylphophoryl azide (1.4 ml, 2.8 mmol, 1.3 eq). The mixture was stirred under nitrogen at 0° C. for 30 minutes, then warmed to RT and stirring continued for a further 2 hours. The reaction mixture was concentrated under vacuum and purified by flash chromatography (90/10-60/40 Iso-hexane/EtOAc) to afford the title compound as white solid (265 mg, yield=78%). 1H NMR (400 MHz, CDCl$_3$) δ 9.14 (d, 1H, J=1.2); 8.50 (dt, 1H, J=1.2, 0.4), 2.62 (s, 3H, broad).

Step 3

1-[5-Chloro-2-(2-dimethylamino-ethoxy)-phenyl]-3-pyrazin-2-yl-urea

In the appropriate vial, a solution of Pyrazine-2-carbonyl azide in DCM was irradiated at 110° C. for 5 minutes in the Personal Smith Synthesiser. The addition of a solution of 5-Chloro-2-(2-dimethylamino-ethoxy)-phenylamine (1,2 eq) in DCM followed and the reaction mixture irradiated at 110° C. for a further 5 minutes. The desired urea precipitate from the reaction mixture was filtrated and washed with DCM (3×150 ml) and ether (3×150 ml) to yield a white solid. (yield=83%) NMR (DMSO-d6) δ 10.6 (s, 1H, broad); 10.39 (s, 1H); 8.71 (s, 1H, broad); 8.3 (d, 1H, J=2.2); 8.29 (dd, 1H, J=2.7, 1.6), 8.26 (d, 1H, J=2.7), 7.05 (d, 1H, J=8.6), 7.02 (dd, 1H, J=8.6, 2.2), 4.10 (t, 2H, J=6.2). 2.40 (t, 2H, J=6.2), 2.19 (s, 6H). LCMS: method A, RT=2.5 min, [MH$^+$=336].

Example 3

1-[5-Chloro-2-(2-dimethylamino-ethoxy)-phenyl]-3-(5-methyl-pyrazin-2-yl)-urea

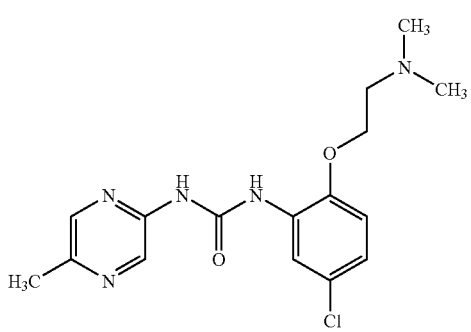

The title compound was prepared from the appropriate reagents, using a procedure similar to that described in Example 2. 1H NMR (400 MHz, DMSO-d6) δ 10.25 (s, 1H, broad); 10.23 (s, 1H); 8.67 (s, 1H, broad); 8.29 (d, 1H, J=2.6); 8.19 (m, 1H) 7.10 (d, 1H, J=8.7); 7.02 (dd, 1H, J=8.7, 2.6), 4.16 (t, 2H, J=6), 2.74 (t, 2H, J=6), 2.43 (s, 3H), 2.22 (s, 6H). LCMS: method A, RT=0.5 min and 2.16 min, [MH$^+$=350].

Example 4

1-(5-Chloro-2,4-dimethoxy-phenyl)-3-pyrazin-2-yl-urea

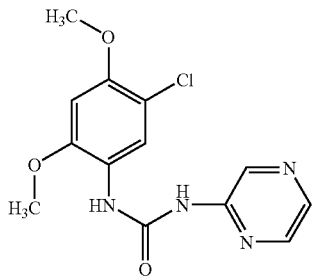

The title compound was prepared from the appropriate reagents, using a procedure similar to that described in Example 2. 1H NMR (400 MHz, DMSO-d6) δ 10.08 (s, 1H,); 9.99 (s, 1H, broad); 8.87 (s, 1H); 8.32 (dd, 1H, J=2.7, 1.6), 8.25 (d, 1H, J=2.7); 8.19 (s, 1H); 6.89 (s, 1H); 3.96 (s, 3H); 3.96 (s, 3H). LCMS: method A, RT=2.81 min, [MH$^+$=309].

Example 5

1-[5-Chloro-2-(2-morpholin-4-yl-ethoxy)-phenyl]-3-pyrazin-2-yl-urea

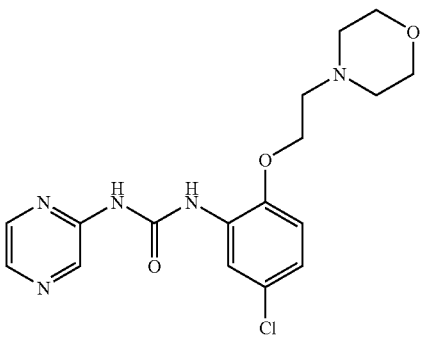

The title compound was prepared from the appropriate reagents, using a procedure similar to that described in Example 2. 1H NMR (400 MHz, DMSO-d6) δ 10.4 (s, 1H, broad); 10.38 (s, 1H); 8.77 (s, 1H); 8.31 (dd, 1H, J=2.74, 1.5); 8.29 (d, 1H, J=2.7, ); 8.28 (d, 1H, J=2.7); 7.12(d, 1H, J=8.6); 7.03 (dd, 1H, J=8.6, 2.7); 4.22 (t, 2H, J=6.0); 3.53(t, 4H, J=4.4); 2.81 (t, 2H, J=6.0); 3.53 (t, 4H, J=4.2). LCMS: method B, RT=3.52 min, [MH$^+$=377].

Example 6

1-(5-Chloro-2-methoxy-phenyl)-3-pyrazin-2-yl-urea

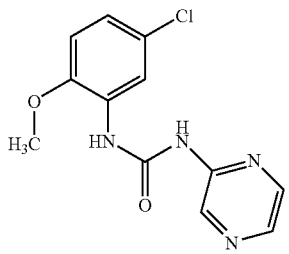

The title compound was prepared from the appropriate reagents, using a procedure similar to that described in Example 2. 1H NMR (400 MHz, DMSO-d6) δ 10.31 (s, 1.5H, broad); 8.96 (s, 1H,); 8.42 (dd, 1H, J=2.5, 1.5); 8.34 (d, 2H, J=2.5); 7.15 (d, 1H, J=8.5); 7.12 (dd, 1H, J=8.5, 2.2); 3.99 (s, 3H).). LCMS: method A, RT=2.89 min, [MH$^+$=279].

Example 7

1-[5-Chloro-2-(3-methyl-butoxy)-phenyl]-3-pyrazin-2-yl-urea

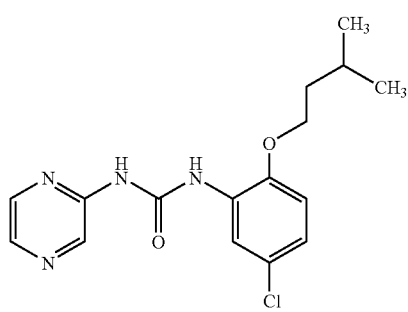

The title compound was prepared from the appropriate reagents, using a procedure similar to that described in Example 2. 1H NMR (400 MHz, DMSO-d6) δ 10.5 (s, 1H, broad); 10.39 (s, 1H); 8.74 (s, 1H); 8.29 (d, 1H, J=2.6); 8.28 (d, 1H, J=2.7), 8.24 (dd, 1H, J=2.7, 1.5), 7.10 (d, 1H, J=8.6); 7.03 (dd, 1H, J=8.6, 2.6); 4.10 (t, 2H, J=6.5); 1.88–1.78 (m, 1H), 1.73 (td, 2H, J=6.6); 0.94 (d, 6H, J=6.4). LCMS: method A, RT=3.61 min, [MH+=335].

Example 8

1-(2-Methoxy-5-methyl-phenyl)-3-pyrazin-2-yl-urea

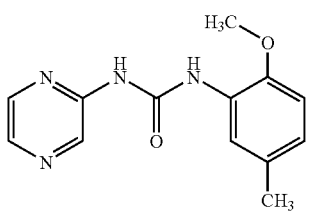

The title compound was prepared from the appropriate reagents, using a procedure similar to that described in Example 2. 1H NMR (400 MHz, DMSO-d6) δ 10.09 (s, 1H, broad); 9.99 (s, 1H, broad); 8.89 (s, 1H,); 8.325 (dd, 1H, J=2.7, 1.6); 8.23 (d, 1H, J=2.7); 8.02(d, 1H, J=2); 6.92 (d, 1H, J=8.5); 6.80 (ddt, 1H, J=8.5, 2.2, 0.6); 3.86 (s, 3H); 2.25 (s, 3H). LCMS: method A, RT=2.8 min, [MH$^+$=259].

Example 9

1-Pyrazin-2-yl-3-(2-trifluoromethoxy-phenyl)-urea

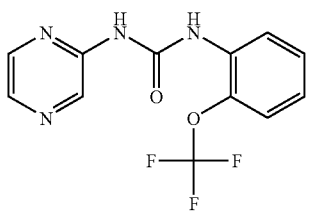

The title compound was prepared from the appropriate reagents, using a procedure similar to that described in Example 2. 1H NMR (400 MHz, DMSO-d6) δ 10.3 (s, 1H, broad); 10.12 (s, 1H); 8.64 (s, 1H); 8.17 (d, 1H, J=8.3); 8.09 (d, 1H, J=2.7); 8.07 (dd, 1H, J=2.7, 1.2); 7.24 (d, 1H, J=8.3); 7.20 (ddd, 1H, J=8.4, 8.4, 1.2); 6.97 (ddd, 1H). LCMS: method A, RT=2.98 min, [MH$^+$=299].

Example 10

1-(5-Chloro-2-methyl-phenyl)-3-pyrazin-2-yl-urea

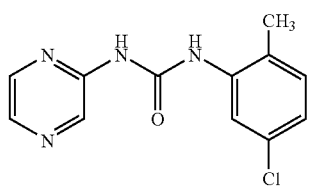

The title compound was prepared from the appropriate reagents, using a procedure similar to that described in Example 2. 1H NMR (400 MHz, DMSO-d6) δ 10.03 (s, 1H); 9.69 (s, 1H, broad); 8.75 (s, 1H,); 8.20 (dd, 1H, J=2.7, 1.6); 8.14 (d, 1H, J=2.7); 8.02–8.012 (m, 1H); 7.12 (d, 1H, J=8.0); 6.91 (dd, 1H, J=8.5, 2.7); 2.15 (s, 3H). LCMS: method B, RT=3.38 min, [MH$^+$=263].

Example 11

N-[4-Methoxy-3-(3-pyrazin-2-yl-ureido)-phenyl]-acetamide

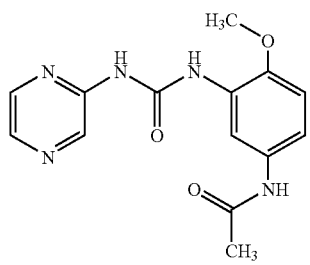

The title compound was prepared from the appropriate reagents, using a procedure similar to that described in Example 2. 1 H NMR (400 MHz, DMSO-d6) δ 10.14 (s, 1H); 10.04 (s, 1H, broad); 9.83 (s, 1H); 8.89 (s, 1H); 8.33 (dd, 1H, J=2.7, 1.5); 8.27 (d, 1H, J=2.4); 8.24 (d, 1H, J=2.7); 7.44 (dd, 1H, J=8.9, 2.6); 6.95 (d, 1H, J=8.9); 3.87 (s, 3H); 2.0 (s, 3H). LMCS: method A, RT=2.38 min, [MH$^+$=302].

Example 12

4-Methoxy-3-(3-pyrazin-2-yl-ureido)-benzoic acid methyl ester

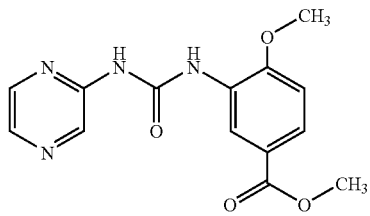

The title compound was prepared from the appropriate reagents, using a procedure similar to that described in Example 2. 1H NMR (400 MHz, DMSO-d6) δ 10.19 (s, 2H); 8.91 (s, 1H); 8.84 (d, 1H, J=2.2); 8.35 (dd, 1H, J=2.7, 1.6); 8.26 (d, 1H, J=2.7); 7.68 (dd, 1H, J=8.6, 2.1); 7.17 (d, 1H, J=8.6); 4.0 (s, 3H); 3.83 (s, 3H). LCMS: method A, RT=3.00 min, [MH$^+$=303].

Example 13

1-(2-Methoxy-5-trifluoromethyl-phenyl)-3-pyrazin-2-yl-urea

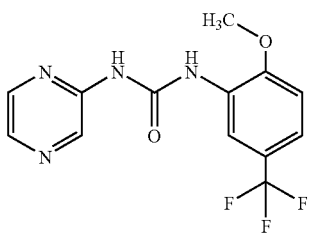

The title compound was prepared from the appropriate reagents, using a procedure similar to that described in Example 2. 1H NMR (400 MHz, DMSO-d6) δ 10.30 (s, 1H, broad); 10.25 (s, 1H); 8.91 (s, 1H); 8.58 (d, 1H, J=2.2); 8.35 (dd, 1H, J=2.6, 1.6); 8.27 (d, 1H, J=2.7); 7.39 (dd, 1H, J=8.6, 2.1); 7.24 (d, 1H, J=8.6); 4.0 (s, 3H). LCMS: method B, RT=3.52 min, [MH$^+$=213].

Example 14

1-(2,4-Dimethoxy-phenyl)-3-pyrazin-2-yl-urea

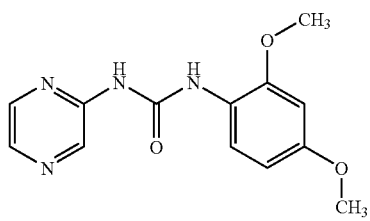

The title compound was prepared from the appropriate reagents, using a procedure similar to that described in Example 2. 1H NMR (400 MHz, DMSO-d6) δ 9.96 (s, 1H); 9.78 (s, 1H, broad); 8.88 (d, 1H, J=1.2); 8.30 (dd, 1H, J=2.7, 1.2); 8.22 (d, 1H, J=2.7); 7.98 (d, 1H, J=8.8); 6.64 (d, 1H, J=2.7); 6.5 (dd, 1H, J=8.6, 2.7); 3.88 (s, 3H); 3.74 (s, 3H). LMCS: method A, RT=3.47, [MH$^+$=243].

Example 15

1-(2-Chloro-5-methoxy-phenyl)-3-pyrazin-2-yl-urea

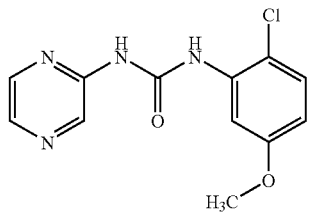

The title compound was prepared from the appropriate reagents, using a procedure similar to that described in Example 2. 1H NMR (400 MHz, DMSO-d6) δ 10.39 (s, 1H, broad); 10.33 (s, 1H); 8.83 (s, 1H); 8.34 (dd, 1H, J=2.6, 1.5); 8.27 (d, 1H, J=2.6); 7.94 (d, 1H, J=2.9); 7.40 (d, 1H, J=8.9); 6.69 (dd, 1H, J=8.9, 2.9); 3.76 (s, 3H). LCMS: method A, RT=2.88, [MH$^+$=279].

Example 16

1-(5-Chloro-2-methoxy-phenyl)-3-pyrimidin-4-yl-urea

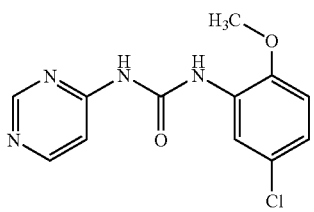

The title compound was prepared from the appropriate reagents, using a procedure similar to that described in Example 2. 1H NMR (400 MHz, DMSO-d6) δ 10.58 (s, 1H, broad); 10.36 (s, 1H); 8.86 (d, 1H, J=1.1); 8.56 (d, 1H, J=5.8); 8.25 (dd, 1H, J=1.1, 1.5); 7.48 (d, 1H, J=5.5); 7.17–7.09 (m, 2H); 3.92 (s, 3H). LCMS: method A, RT=2.79, [MH$^+$=279].

Example 17

1-(2-Methoxy-phenyl)-3-pyrazin-2-yl-urea

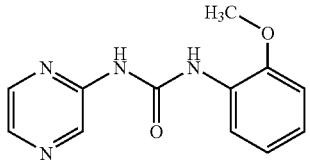

The title compound was prepared from the appropriate reagents, using a procedure similar to that described in Example 2. 1H NMR (400 MHz, DMSO-d6) δ 9.98 (s, 1H); 9.90 (s, 1H, broad); 8.75 (s, 1H); 8.19 (dd, 1H, J=2.5, 1.5); 8.10 (d, 1H, J=2.5); 8.03 (dd, 1H, J=7.3, 1.1); 6.91 (dd, 1H, J=8.0, 1.5); 6.87 (ddd, 1H, J=8.0, 7.3, 1.5); 6.78 (ddd, 1H, J=8.0, 7.3, 1.5); 3.76 (s, 3H). LCMS: method B, RT=3.16, [MH+=245].

Example 18

1-(3-Chloro-4-methoxy-phenyl)-3-pyrazin-2-yl-urea

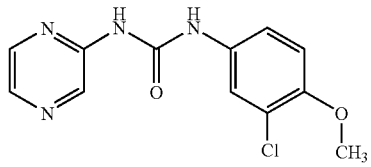

The title compound was prepared from the appropriate reagents, using a procedure similar to that described in Example 2. 1H NMR (400 MHz, DMSO-d6) δ 9.65 (s, 1H); 9.57 (s, 1H); 8.99 (d, 1H, J=1.5); 8.31 (dd, 1H, J=2.7, 1.6); 8.25 (d, 1H, J=2.5); 7.71 (d, 1H, J=2.5); 7.33 (dd, 1H, J=8.9, 2.5); 7.12 (d, 1H, J=8.9); 3.83 (s, 3H). LCMS: method A, RT=3.37, [MH$^+$=279].

Example 19

1-(3-Chloro-phenyl)-3-pyrazin-2-yl-urea

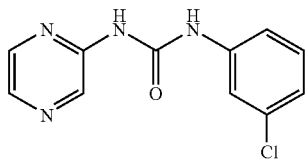

The title compound was prepared from the appropriate reagents, using a procedure similar to that described in Example 2. 1H NMR (400 MHz, DMSO-d6) δ 9.96 (s, 1H); 9.78 (s, 1H); 9.17 (s, 1H); 8.47 (dd, 1H, J=2.5, 1.5); 8.41 (d, 1H, J=2.7); 7.90 (dd, 1H, J=2.5, 1.5); 7.46–7.49 (m, 2H); );7.21–7.25 (m, 1H) method B, RT=3.31, [MH$^+$=249, MNa$^+$=271].

Example 20

1-(3-Chloro-phenyl)-3-pyrazin-2-yl-urea

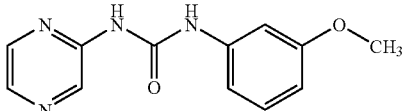

The title compound was prepared from the appropriate reagents, using a procedure similar to that described in Example 2. 1H NMR (400 MHz, DMSO-d6) δ 9.62 (s, 1H); 9.52 (s, 1H); 9.04 (d, 1H, J=1.5); 8.32 (dd, 1H, J=2.6, 1.5); 8.26 (d, 1H, J=2.6); 7.20–7.24 (m, 2H); 6.99 (ddd, 1H, J=8.2, 1, 2.6); 6.62 (ddd, 1H, J=8.2, 2.6, 1); 3.75 (s, 3H). LCMS: method A, RT=2.67, [MH$^+$=245].

Example 21

1-(4-Piperidin-1-yl-phenyl)-3-pyrazin-2-yl-urea

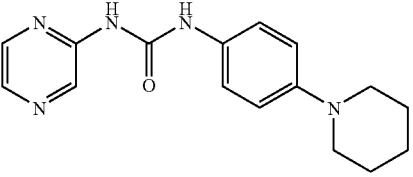

The title compound was prepared from the appropriate reagents, using a procedure similar to that described in Example 2. 1H NMR (400 MHz, DMSO-d6) δ 9.25 (s, 1H); 9.20 (s, 1H); 8.78 (s,1 H); 8.07 (dd, 1H, J=2.5, 1.5); 8.00 (d, 1H, J=2.7); 7.106 (dd, 2H, J=9.0, 2.7); 6.67 (dd, 2H, J=9.0, 2.7); 2.83 (t, 1H, J=5.3); 1.37–1.42 (m, 4H); 1.27–1.31 (m, 2H). LCMS: method A, RT=0.74, 2.28, [MH$^+$=203].

Example 22

1-(4-Piperidin-1-yl-phenyl)-3-pyrazin-2-yl-urea

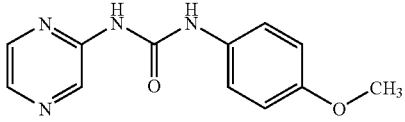

The title compound was prepared from the appropriate reagents, using a procedure similar to that described in Example 2. 1H NMR (400 MHz, DMSO-d6) δ 9.49 (s, 2H, broad); 9.00 (d, 1H, J=1.46), 8.30 (dd, 1H, J=1.46, 2.56), 8.23 (d, 1H, J=2.56), 7.39–7.43 (m, 2H), 6.88–6.93 (m, 2H), 3.73 (s, 3H).

Example 23

1,3-Di-pyrazin-2-yl-urea

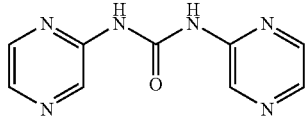

The title compound was prepared from the appropriate reagents, using a procedure similar to that described in Example 2. 1H NMR (400 MHz, DMSO-d6) δ 10.41 (s, 2H, broad); 9.28 (s, 2H), 8.81 (dd, 2H, J=2.5, 1.5), 8.47 (d, 2H, J=2.56).

Example 24

1-Benzo[1,3]dioxol-5-yl-3-pyrazin-2-yl-urea

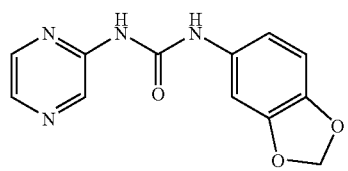

The title compound was prepared from the appropriate reagents, using a procedure similar to that described in Example 2. 1H NMR (400 MHz, DMSO-d6) δ 9.38 (s, 1H, broad), 9.32 (s, 1H, broad), 8.8 (s, 1H, broad), 8.1 (dd, 1H, J=2.3, 1.5), 8.05 (d, 1H, J=2.56), 7.05 (d, 1H, J=2.0), 6.68 (d, 1H, J=8.35); 6.64 (dd, 1H, J=8.3, 2.0), 5.80 (s, 2H).

Example 25

1-[5-Chloro-2-(3-dimethylamino-propoxy)-phenyl]-3-(5-methyl-pyrazin-2-yl)-urea

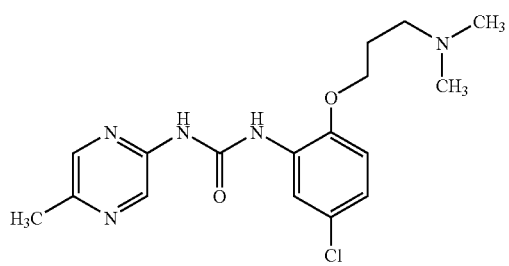

The title compound was prepared from the appropriate reagents, using a procedure similar to that described in Example 2. 1H NMR (400 MHz, DMSO-d6) δ 10.25 (s, 1H, broad); 8.62 (s, 1H); 8.31 (d, 1H, J=2.2); 8.20 (s, 1H, broad); 7.01 (d, 1H, J=8.7); 7.04 (dd, 1H, J=8.7, 2.2); 4.10 (t, 2H, J=6.2); 2.42 (s, 3H); 2.40 (t, 2H, J=7.3); 2.13 (s, 6H); 1.97 (td, 2H, J=7.3, 6.2). LCMS: method B, RT=4.14 min, [MH+=364].

Example 26

1-[2-(2-Aziridin-1-yl-ethoxy)-5-chloro-phenyl]-3-pyrazin-2-yl-urea

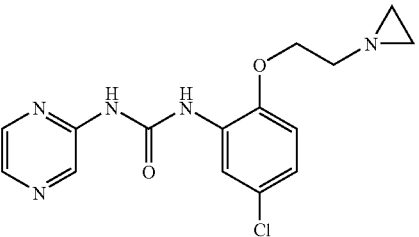

The title compound was prepared from the appropriate reagents, using a procedure similar to that described in Example 2. 1H NMR (400 MHz, DMSO-d6) δ 10.59 (s, 1H, broad), 8.74 (s, 1H), 8.32 (dd, 1H, J=2.7, 1.5), 8.29 (d, 1H, J=2.56), 8.26 (d, 1H, J=2.7), 7.10 (d, 1H, J=8.7), 7.04 (dd, 1H, J=2.56), 4.20 (t, 2H, J=5.5), 2.63 (t, 2H, J=5.5), 1.62 (m, 2H)

Example 27

1-[5-Chloro-2-(pyridin-3-ylmethoxy)-phenyl]-3-pyrazin-2-yl-urea

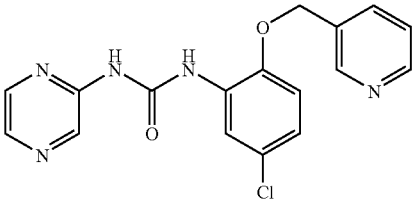

The title compound was prepared from the appropriate reagents, using a procedure similar to that described in Example 2. 1H NMR (400 MHz, DMSO-d6) δ 10.55 (s, 1H, broad), 10.35 (s, 1H), 8.78 (dd, 1H, J=2.19, 0.54), 8.69 (s, 1H, broad), 8.62 (dd, 1H, J=1.64, 4.75), 8.32 (d, 1H, J=2.56), 8.16 (d, 1H, J=2.74), 7.9 (ddd, 1H, J=5.5, 4.7, 0.7), 7.61 (s, 1H, broad), 7.48 (ddd, 1H, 7.7, 4.7, 0.7), 7.24 (d, 1H, J=8.7), 7.08 (dd, 1H, 2.7, 8.7), 5.27 (s, 2H).

Example 28

1-[5-Chloro-2-amino-propoxy)-phenyl]-3-(5-methyl-pyrazin-2-yl)-urea

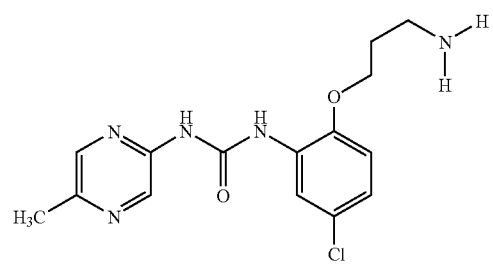

Step 1

[3-(4-Chloro-2-nitro-phenoxy)-propyl]-carbamic acid tert-butyl ester

A solution of (3-Hydroxy-propyl)-carbamic acid tert-butyl ester (11 mmoles, 1.88 ml) in THF (20 ml) was added to a suspension of sodium hydride 50% grade (23 mmoles, 1.058 g) in THF (20 ml) and stirred at 50° C for 1 hour. Following cooling to 0° C., 4-Chloro-1-fluoro-2-nitro-benzene was added and the mixture stirred at RT overnight. After quenching with water, the organic layer was separated and the aqueous layer was extracted several times with Ethyl acetate. The combined organic layers were washed with water then brine, and dried over sodium sulfate. The crude reaction was purified by flash chromatography to afford [3-(4-Chloro-2-nitro-phenoxy)-propyl]-carbamic acid tert-butyl ester.

NMR: 1H NMR (400 MHz, DMSO-d6) δ 8.014 (d, 1H, J=2.74); 7.71 (dd, 1H, J=9.1, 2.7); 7.37 (d, 1H, J=9.1); 6.85 (t, broad, 1H, J=5.8); 4.16 (t, 2H, J=6.03); 3.06 (td, 2H, J=5.8, 6.7), 1.85–1.79 (m, 2H); 1.36 (s, 9H). LCMS: method B, RT=3.52 min, [MH$^+$=331].

Step 2

[3-(2-Amino-4-chloro-phenoxy)-propyl]-carbamic acid tert-butyl ester

A solution of [3-(4-Chloro-2-nitro-phenoxy)-propyl]-carbamic acid tert-butyl ester (1.78 g) was hydrogenated in ethanol (50 ml) in presence of Platinum oxide (178 mg) for 2 hours. The mixture was filtrated over a pad of celite and concentrated under vacuum. The crude reaction was purified by flash chromatography to afford [3-(2-Amino-4-chloro-phenoxy)-propyl]-carbamic acid tert-butyl ester (1.39 g, yield=86%) as a viscous oil which solidified slowly:

NMR: 1H NMR (400 MHz, DMSO-d6) δ 6.80 (t, broad, 1H, J=5.4); 6.67 (d, 1H, J=8.4); 6.56 (d, 1H, J=2.74); 6.41 (dd, 1H, J=8.4, 2.7); 4.92 (s, broad, 2H); 3.86 (t, 2H, J=6.2); 3.03 (td, 2H, J=5.4, 6.0); 1.79–7.73 (m, 2H); 1.31 (s, 9H). LCMS: method B, RT=3.28 min, [MH$^+$=301].

Step 3

(3-{4-Chloro-2-[3-(5-methyl-pyrazin-2-yl)-ureido]-phenoxy}-propyl)-carbamic acid tert-butyl ester]

Using a procedure similar to that described in example 2 step (2 and 3), the desired urea was obtained as a light beige solid.

1H NMR (400 MHz, DMSO-d6) δ 10.21 (s, broad, 1H); 8.41 (s, 1H, broad); 8.31–8.30 (m, 1H); 8.17 (s, 1H, broad); 7.03–7.029 (m, 2H); 6.92–6.91 (t, 1H, broad); 4.086 (t, 2H, J=6.2); 3.19–3.14 (m, 2H); 2.44 (s, 3H); 1.92–1.95 (m, 2H); 1.36 (s, 9H). LCMS: method B, RT=3.37 min, [MH$^+$=436].

Step 4

1-[5-Chloro-2-amino-propoxy)-phenyl]-3-(5-methyl-pyrazin-2-yl)-urea

A suspension of the urea in dioxane was treated with a 4M HCl Dioxane solution for 1 hour. The solvent was evaporated under vacuum and the residue was triturated with a small portion of MeOH and filtrated to afford a light beige solid.

1H NMR (400 MHz, DMSO-d6) δ: 10.36 (s, 1H); 10.30–10.1 (s, 1H, broad); 8.74 (s, 1H, broad); 8.296–8.299 (m, 1H); 8.05 (m, 2H); 7.055–7.052 (m, 2H); 4.18 (t, 2H, J=6.22); 3.08–3.03 (m, 2H), 2.45 (s, 3H); 2.19–2.13 (m, 2H). LCMS: method B, RT=3.37 min, [MH$^+$=436].

Example 29

1-[2-(3-Amino-propoxy)-5-chloro-phenyl]-3-pyrazin-2-yl-urea

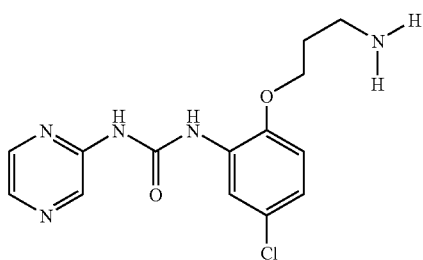

The title compound was prepared from the appropriate reagents, using a procedure similar to that described in example 28.

1H NMR (400 MHz, DMSO-d6) δ: 10.48 (s, 1H); 10.38–10.12 (s, broad, 1H), 8.84 (s, 1H); 8.34 (dd, 1H, J=1.64, 1.28); 8.29 (m, 1H); 8.27 (d, 1H, J=2.7); 8.00 (s, broad, 2H); 7.08 (m, 2H); 4.18 (t, 2H, J=6.2); 3.10–3.00 (m, 2H); 2.20–2.10 (m, 2H). LCMS: method B, RT=1.81 min, [MH$^+$=322].

Example 30

1-[5-Chloro-2-(3-dimethylamino-propoxy)-phenyl]-3-quinoxalin-2-yl-urea

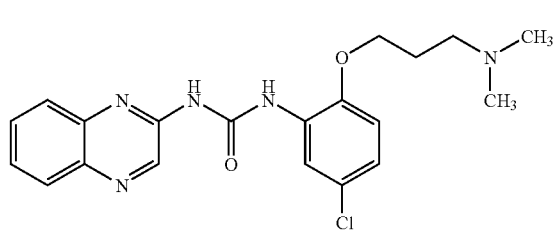

The title compound was prepared from the appropriate reagents, using a procedure similar to that described in example 1.

1H NMR (400 MHz, DMSO-d6) δ: 10.29 (s, 2H, broad); 10.18 (s, 1H, broad); 9.05 (s, 1H, broad); 8.30 (d, 1H, J=2.5); 8.02 (d, 1H, J=8.0); 7.86–7.51 (m, 2H); 7.69 (dd, 1H, J=8.2, 4.2); 7.16 (d, 1H, J=8.7); 7.11 (dd, 1H, J=8.7, 2.5); 4.30 (t, 2H, J=6.4); 3.23–3.19 (m, 2H); 2.66 (s, 6H); 2.25–2.18 (m, 2H). LCMS: method A, RT=3.56 min, [MH+=400].

Example 31

1-[2-(3-Amino-propoxy)-5-chloro-phenyl]-3-quinoxalin-2-yl-urea

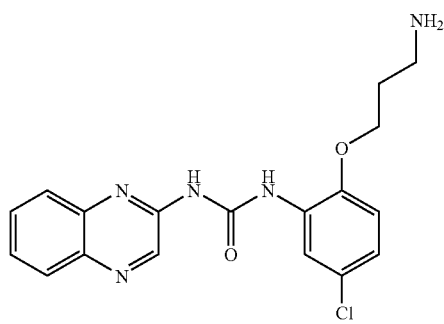

The title compound was prepared from the appropriate reagents, using a procedure similar to that described in example 28.

1H NMR (400 MHz, DMSO-d6) δ: 10.86 (s, 2H, Broad); 9.07 (s, 1H, broad); 8.34 (d, 1H, J=2.5); 8.02 (d, 1H, J=8.2); 7.96–7.90 (s, 1H, broad); 7.87–7.82 (m, 2H); 7.69 (ddd, 1H, J=8.2, 6, 2.2); 7.17 (d, 1H, J=8.7); 7.11 (dd, 1H, J=2.5, 8.7); 4.35 (t, 2H, J=6.2); 2.96–2.92 (m, 2H); 2.12 (m, 2H). LCMS: method B, RT=2.02 min, [MH+=372].

Example 32

1-[2-(2-Amino-ethoxy)-5-chloro-phenyl]-3-pyrazin-2-yl-urea

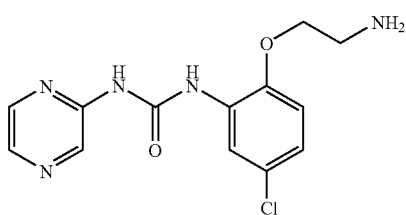

The title compound was prepared from the appropriate reagents, using a procedure similar to that described in example 28

1H NMR (400 MHz, DMSO-d6) δ: 10.66 (s, 1H); 9.80 (s, 1H); 9.19 (d, 1H, J=1.3); 8.47–8.39 (s, 2H, broad); 8.33 (dd, 1H, J=0.9, 1.6); 8.30 (m, 1H); 8.27 (d, 1H, J=2.56); 7.05 (m, 2H); 4.23 (t, 2H, J=5); 3.33–3.31 (m, 2H). LCMS: method B, RT=1.75 min, [MH+=308].

Example 33

1-[2-(4-Amino-butoxy)-5-chloro-phenyl]-3-(5-methyl-pyrazin-2-yl)-urea

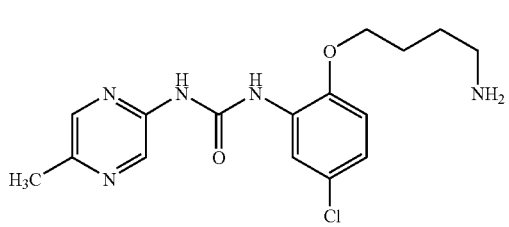

The title compound was prepared from the appropriate reagents, using a procedure similar to that described in example 28.

1H NMR (400 MHz, DMSO-d6) δ: 10.34 (s, 1H); 8.73 (s, 1H); 8.31 (d, 1H, J=2.4); 8.20 (s, 1H); 7.94 (s, 2H); 7.09 (d, 1H, J=8.8); 7.04 (dd, 1H, J=8.8, 2.4); 4.13 (t, 2H, J=6.03); 2.93–2.85 (m, 2H); 2.46 (s, 3H); 1.97–1.90 (m, 2H); 1.83–1.78 (m, 2H). LCMS: method B, RT=1.94 min, [MH+=349].

Example 34

1-[5-Chloro-2-amino-propoxy)-phenyl]-3-(6-methoxy-pyrazin-2-yl)-urea

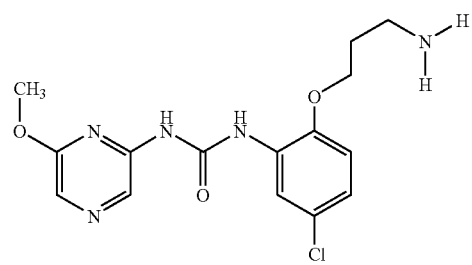

The title compound was prepared from the appropriate reagents, using a procedure similar to that described in example 28, the desired urea was obtained as a light beige solid.

1H NMR (400 MHz, DMSO-d6) δ: 10.31 (s, broad, 1H); 9.06 (s, 1H); 8.74 (s, 1H); 8.21 (s, 1H); 8.11 (s, 1H, broad); 7.91 (m, 2H); 7.031–7.034 (m, 2H); 4.15 (t, 2H, J=6.04) 3.88 (s, 3H); 3.05–3.015 (m, 2H); 2.13–2.06 (m, 2H). LCMS: method A, RT=1.94 min, [MH+=351].

Example 35

1-[5-Methyl-2-(3-dimethylamino-propoxy)-phenyl]-3-pyrazin-2-yl-urea

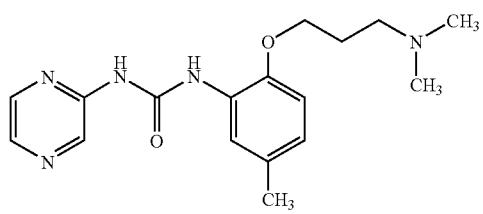

The title compound was prepared from the appropriate reagents, using a procedure similar to that described in example 1.

1H NMR (400 MHz, DMSO-d6) δ: 10.32 (s, 1H, broad); 10.31 (s, 1H, broad); 9.9 (s, 1H, broad); 8.82 (s, 1H); 8.29–8.27 (m, 1H); 8.16 (d, 1H, J=2.7); 7.93 (m, 1H); 6.86 (d, 1H, J=8.2); 6.73 (dd, 1H, J=8.2, 2.19); 4.04 (t, 2H, J=6.2); 3.24–3.19 (m, 2H); 2.71–2.69 ($d_{app}$, 6H); 2.17 (s, 3H); 2.20–2.11 (m, 2H). LCMS: method B, RT=3.56 min, [MH$^+$=330].

Example 35A

1-[2-(3-Amino-2,2-dimethyl-propoxy)-5-chloro-phenyl]-3-(5-methyl-pyrazin-2-yl)-urea

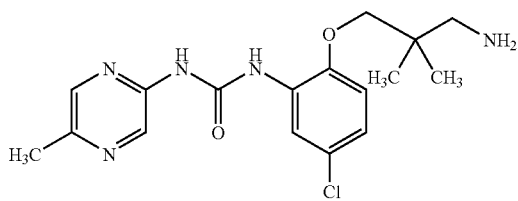

The title compound was prepared from the appropriate reagents, using a procedure similar to that described in example 1. Proton NMR: dH (400 MHz; MeOD) 8.52 (1H, s, CH), 8.16 (1H, s, CH), 7.98 (1H, d, CH), 6.90 (2H, m, 2×CH), 3.78 (2H, s, CH2), 2.99 (2H, s, CH2), 2.40 (3H, s, CH3), 1.09 (6H, s, 2×CH3). MS: [ES+]364; [ES−]=362. LCMS: method B.

Example 35B

6-{3-[2-(3-Amino-propoxy)-5-chloro-phenyl]-ureido}-nicotinamide

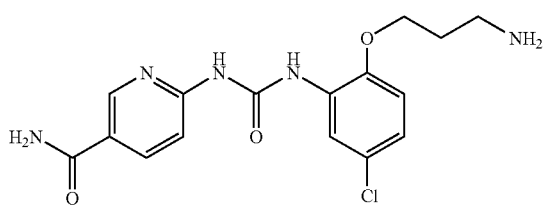

The title compound was prepared from the appropriate reagents, using a procedure similar to that described in example 1. Proton NMR: dH (400 MHz; MeOD) 8.65 (1H, d, CH), 8.44 (1H, d, CH), 8.16 (1H, d, CH), 7.32 (1H, d, CH), 6.92 (2H, m, 2×CH), 4.10 (2H, t, CH2), 3.15 (2H, t, CH2), 2.19 (2H, q, CH2). MS: [ES+]364; [ES−]=362. LCMS: method B.

Example 35C

1-[2-(3-Amino-propoxy)-5-chloro-phenyl]-3-(5-cyano-pyridin-2-yl)-urea

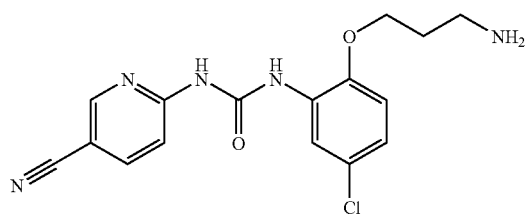

Proton NMR: dH (400 MHz; DMSO) 10.52 (1H, s, NH), 10.26 (1H, br, NH), 8.53 (1H, d, CH), 8.07 (1H, t, CH), 7.99 (1H, dd, CH), 7.43 (1H, d, CH), 6.87 (2H, d, 2×CH), 4.00 (2H, t, CH2), 2.83 (2H, m, CH2), 1.95 (2H, m, CH2). MS: [ES+]=346. LCMS: method B.

Example 35D

1-[5-Chloro-2-(3-cyclobutylamino-propoxy)-phenyl]-3-(5-methyl-pyrazin-2-1)-urea

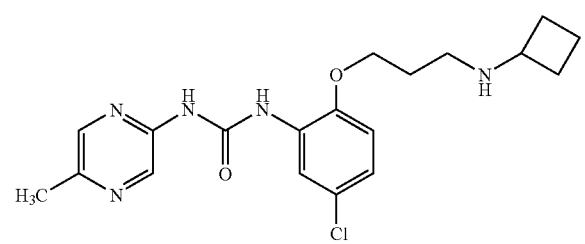

NMR: 1H (400 MHz; DMSO-D6): 10.15 (s, 1H, Broad); 9.1–8.9 (2S, 2H, broad); 8.56 (s, 1H, broad); 8.08 (tapp, 1H, J=1.3); 8.05 (s, 1H, broad); 6.85 (dapp, broad); 3.98 (t, 2H, J=6.04); 3.52–3.42 (m, 1H); 2.85–2.65 (m, 2H); 2.25 (s, 3H); 2.03–1.9 (m, 6H); 1.613–1.517 (m, 2H). LCMS, Method A: Rt=1.96 Min [MH+=390].

LCMS Method A

Analysed using a Waters Symmetry [C8, 50×4.6 mm, 3.5 uM] eluting with acetonitrile/water/0.1% formic acid (5–95% acetonitrile) for 5 minutes with a flow rate of 1.5 ml/min.

LCMS Method B

Analysed using a Waters Symmetry [C8, 50×4.6 mm, 3.5 uM] eluting with methanol/water/10 mM Ammonium acetate (5–95% methanol) for 5 minutes with a flow rate of 1.5 ml/min.

NMR

NMR data was recorded on a Bruker NMR spectrometer (400 MHz).

LCMS Method B

Analysed using a Waters Symmetry [C8, 50×4.6 mm, 3.5 uM] eluting with methanol/water/10 mM Ammonium acetate (5–95% methanol) for 5 minutes with a flow rate of 1.5 ml/min.

NMR

NMR data was recorded on a Bruker NMR spectrometer (400 MHz).

Example 36

Biological Assays

Chk1 Expression & Purification:

Recombinant human Chk1 was expressed as a fusion protein with glutathione S-transferase at the amino-terminus (GST-Chk1) using standard baculovirus vectors and (Bac-to-Bac®) insect cell expression system purchased from GIBCO™ Invitrogen. Recombinant protein expressed in insect cells was purified using glutathione sepharose (Amersham Biotech) using standard procedures described by the manufacturer.

Chk1 Fluorescence Polarization Assays:

Chk1 kinase inhibitors were identified using fluorescence polarization to monitor kinase activity. This assay utilized 10 nM GST-Chk1 and contained 5 mM 2-(N-Morpholino) ethanesulfonic acid (MES, pH 6.5), 5 mM magnesium chloride ($MgCl_2$), 0.05% Tween®-20, 1 uM adenosine 5' triphosphate (ATP), 2 mM 1,4-Dithio-DL-threitol (DTT), 1 uM peptide substrate (Biotin-ILSRRPSYRKILND-free acid) (SEQ ID NO: 1), 10 nM peptide substrate tracer (Fluorescine-GSRRP-pS-YRKI-free acid) (pS=phosphorylated-Serine) (SEQ ID NO: 2), 60 ng anti-phospho-CREB (S133) mouse monoclonal IgG purified on Protein G sepharose from crude mouse ascites purchased from Cell Signaling Technologies (Beverly, Mass.), 4% dimethyl sulfoxide (DMSO) and 30 uM inhibitor. Reactions were incubated at room temperature for 140 minutes and terminated by addition of 25 mM EDTA (pH 8.0). Stopped reactions were incubated for 120 minutes at room temperature and fluorescence polarization values determined using a Molecular Devices/LJL Biosystems Analyst™ AD (Sunnyvale, Calif.) with standard fluorescine settings.

Additonal assays were also used to determine inhibitor potency and ability of inhibitors to compete for ATP binding site of Chk1:

Chk1 SPA filtration Assay:

Assays (25 ul) contained 10 nM GST-Chk1, 10 mM MES, 2 mM DTT, 10 mM $MgCl_2$, 0.025% Tween®-20, 1 uM peptide substrate (Biotin-ILSRRPSYRKILND-free acid) (SEQ ID NO: 1), 1 uM ATP, 0.1 uCi $^{33}$P-γ-ATP (New England Nuclear, NEN) and reacted for 90 minutes at room temperature. Reactions were terminated by adding 55 ul of phosphate buffered saline containing 50 mM EDTA, 6.9 mM ATP, 0.5 mg Scintilation proximity assay (SPA) beads (Amersham Biosciences). Peptide substrate was allowed to bind beads for 10 minutes at room temperature followed by filtration on a Packard GF/B Unifilter plate and washing with phosphate buffered saline. Dried plates were sealed with Topseal™ (NEN) and $^{33}$P incorporated to peptide substrate detected using a Packard Topcount® scintillation counter with standard settings for $^{33}$P.

Chk1 FlashPlate® Kinase Assay:

Assays (25 ul) contained 8.7 nM GST-Chk1, 10 mM MES, 0.1 mM ethylene glycol-bis(β-aminoethylether)-N,N,N',N'-tetracetic acid (EGTA, pH 8.0), 2 mM DTT, 0.05% Tween 20, 3 uM peptide substrate (Biotin-ILSRRPSYR-KILND-free acid) (SEQ ID NO: 1), 1 uM ATP, 0.4 uCi $^{33}$P-γ-ATP (NEN), 4% DMSO. Reactions were incubated for 30 minutes at room temperature, terminated with 50 ul of 50 mM EDTA and 90 ul were transferred to streptavidin-coated FlashPlates® (NEN) and incubated for 1 hour at room temperature. Plates were washed with phosphate buffered salaine containing 0.01% Tween-20 and 10 mM sodium pyrophosphate. Plates were dried, sealed with Topseal™ (NEN) and amount of $^{33}$P incorporated into the peptide substate measure using a Packard Topcount® NXT™ scintillation counter with standard settings.

Chk1 DELFIA® Kinase Assay:

Assays (25 ul) utilized 6.4 nM GST-Chk1 containing 25 mM Tris, pH 8.5, 20% glycerol, 50 mM sodium chloride (NaCl), 0.1% Surfact-Ampsg 20, 1 uM peptide stubstrate (Biotin-GLYRSPSMPEN-amide) (SEQ ID NO: 3), 2 mM DTT, 4% DMSO, 12.5 uM ATP, 5 mM $MgCl_2$ and reacted for 30 minutes at room temperature. Reactions were terminated with 100 ul of Stop buffer containing 1% BSA, 10 mM Tris, pH 8.0, 150 mM NaCl, 100 mM EDTA. Stopped reactions (100 ul) were transferred to 96 well neutravidin plates (Pierce) to capture the biotin-peptide substrate during a 30 minute room temperature incubation. Wells were washed and reacted with 100 ul PerkinElmer Wallac Assay Buffer containing 21.5 ng/ml anti-phospho-Ser216-Cdc25c rabbit polyclonal antibody from Cell Signaling Technology (Beverly, Mass.) and 292 ng/ml europium labeled anti-rabbit-IgG for 1 hour at room temperature. Wells were washed and europium released from the bound antibody by addition of Enhancement Solution (100 ul) (PerkinElmer Wallac) and detected using a Wallac Victor2™ using standard manufacturer settings.

Example 37

Compounds of the Present Invention are Potent Inhibitors of CHK-1

Compounds of the present invention were tested in the Chk1 FlashPlate® kinase assay described above. The results are shown in Table 1 below.

TABLE 1

| Compound | $IC_{50}$ |
| --- | --- |
| Compound from Example 1 | A |
| Compound from Example 2 | A |
| Compound from Example 3 | A |
| Compound from Example 4 | A |
| Compound from Example 5 | B |
| Compound from Example 6 | B |
| Compound from Example 7 | B |
| Compound from Example 8 | B |
| Compound from Example 9 | B |
| Compound from Example 10 | B |
| Compound from Example 11 | B |
| Compound from Example 12 | B |
| Compound from Example 13 | B |
| Compound from Example 14 | B |
| Compound from Example 15 | B |
| Compound from Example 16 | C |
| Compound from Example 17 | C |
| Compound from Example 18 | C |
| Compound from Example 19 | C |

TABLE 1-continued

| Compound | IC$_{50}$ |
|---|---|
| Compound from Example 20 | C |
| Compound from Example 21 | C |
| Compound from Example 22 | C |
| Compound from Example 23 | C |
| Compound from Example 24 | C |
| Compound from Example 25 | A |
| Compound from Example 26 | B |
| Compound from Example 27 | B |

TABLE 1-continued

| Compound | IC$_{50}$ |
|---|---|
| Compound 46 | B |
| Compound 92 | A |
| Compound 109 | A |
| Compound 110 | A |
| Compound 111 | A |
| Compound 112 | A |

A = IC$_{50}$ less than 0.1 µM
B = IC$_{50}$ less than 1.0 µM
C = IC$_{50}$ less than 20.0 µM As can be seen from the data presented in the Table, the disclosed compounds are potent inhibitors of Chk-1.

Example 38

WST Assay Procedure

HT29, HCT116 (5000 cells/well) or other cells were seeded (75 ul) to 96 well clear bottom plates at densities which provide linear growth curves for 72 hours. Cells were cultured under sterile conditions in appropriate media and for HT29 & HCT116 this media was McCoy's 5A containing 10% Fetal Bovine Serum (FBS). Following the initial seeding of cells they are incubated at 37° C., 5% CO$_2$ from 17 to 24 hours at which time the appropriate DNA damaging agents (camptothecins, 5-fluorouracil and etoposid) are added at increasing concentrations to a point which is capable of causing at least 80% cell killing with in 48 hours. Final volume of all DNA damaging agent & compound additions was 25 ul and assays contained <1% DMSO final. At the same time as DNA Damaging agent addition, Chk1 inhibitor was added at fixed concentrations to each DNA damaging agent titration to observe enhancement of cell killing. In addition, toxicity of each Chk1 inhibitor alone was observed. By doing this over a range of Chk1 inhibitor concentrations we were able to identify compounds which maximally enhance (2–30 fold) cell killing by each DNA damaging agent and generated ≦80% cell killing by the compound alone. Cell viability/cell killing under the conditions described above was determined by addition WST reagent (Roche) according to the manufacturer at 47 hours following DNA damage & Chk1 inhibitor addition and following a 3.5 hour or 2.5 hour incubation at 37 C, 5% CO$_2$, OD$_{450}$ was measured. The results from these experiments are shown below in Table 2.

TABLE 2

| Example | R$^1$ | IC$_{50}$ average | 78 nM | 156 nM | Shift 313 nM | 625 nM | 1.25 µM | 2.5 µM |
|---|---|---|---|---|---|---|---|---|
| 30 | —O(—CH$_2$)$_3$N(CH$_3$)$_2$ | 0.019 | nd | nd | nd | nd | 1 | 1.4 |
| 31 | —O(CH$_2$)$_3$NH$_2$ | 0.005 | nd | 1.3 | 1.8 | 2.8 | 4.4 | 6.2 |
| 2 | —O(CH$_2$)$_2$N(CH$_3$)$_2$ | 0.008 | nd | 1 | 1.1 | 1.5 | 1.9 | 2.6 |
| 32 | —O(CH$_2$)$_2$NH$_2$ | 0.016 | nd | nd | nd | nd | 1.2 | 1.4 |
| 25 | —O(CH$_2$)$_3$N(CH$_3$)$_2$ | 0.0045 | nd | 1.1 | 1.7 | 2.5 | 3.3 | 4.4 |
| 28 | —O(CH$_2$)$_3$NH$_2$ | 0.004 | 2.7 | 3.4 | 5.3 | 6.8 | toxic | toxic |
| 1 | —O(CH$_2$)$_3$N(CH$_3$)$_2$ | 0.0035 | nd | 1 | 1.2 | 1.6 | 2.2 | 3.4 |
| 29 | —O(CH$_2$)$_3$NH$_2$ | 0.0025 | 2.5 | 3.1 | 4.5 | 5.0 | toxic | toxic |
| 33 | —O(CH$_2$)$_4$NH$_2$ | 0.003 | 1.8 | 2.4 | 2.7 | 3.1 | toxic | toxic |
| 35 | O—(CH$_2$)$_3$N(CH$_3$)$_2$ | 0.016 | nd | nd | nd | nd | 2.1 | 2.9 |
| 34 | —O(CH$_2$)$_3$NH$_2$ | 0.020 | nd | nd | nd | nd | 2.4 | 3.031 |

Where a shift of 1 is equal to no shift.
Nd = not determined.
*IC$_{50}$ µM for the test compound versus CHK-1

As can be seen from these datas, phenyl urea CHK-1 inhibitors substituted with an —O—T—NH$_2$ group significantly enhance of the activity of the DNA damaging agent compared with other phenyl urea CHK-1 inhibitors.

While this invention has been particularly shown and described with references to preferred embodiments thereof, it will be understood by those skilled in the art that various changes in form and details may be made therein without departing from the scope of the invention encompassed by the appended claims.

What is claimed is:
1. A compound of Formula III:

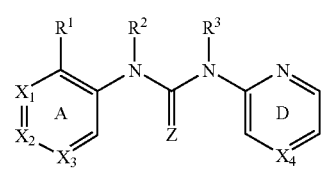

III or a pharmaceutically acceptable salt thereof, wherein:
X$_1$–X$_3$ are;
X$_4$ is N;
Z is O, S, or N—CN;
Ring A is optionally substituted at any substitutable carbon by R$^4$;
R$^1$ is —T—NH$_2$, —V—T—NH$_2$, —T—NHR$^x$, or —V—T—NHR$^x$;
T is a C$_{1-6}$ straight or branched alkylidene chain that is optionally interrupted by —O—, —S—, —N(R$^5$)—, —S(O)—, —SO$_2$—, —C(O)—, —OC(O)—, —N(R$^5$)C(O)—, —C(O)N(R$^5$)—, —SO$_2$N(R$^5$)—, or —N(R$^5$)

SO₂—, wherein the alkylidene chain or a portion thereof is optionally part of a 3–6 membered ring system;

V is —O—, —S—, —N(R⁵)—, —S(O)—, —SO₂—, —C(O)—, —OC(O)—, —N(R⁵)C(O)—, —C(O)N(R⁵)—, —SO₂N(R⁵)—, or —N(R⁵)SO₂—;

R² and R³ are each independently selected from hydrogen, C₁₋₆ alkyl optionally substituted with —N(R⁸)₂, —C(=O)R, —CO₂R, or SO₂R, or R² and R³ taken together with their intervening atoms form an optionally substituted an optionally substituted 5–6 membered ring;

each R⁴ is independently selected from halo, —OR, —SR, —CN, —NO₂, —N(R⁵)₂, —N(R⁵)C(O)R, —N(R⁵)CO₂R, —N(R⁵)C(O)N(R⁵)₂, —C(O)N(R⁵)₂, —C(O)R⁵, —OC(O)N(R⁵)₂, —CO₂R, —SO₂R, —S(O)R, —SO₂N(R⁵)₂, —N(R⁵)SO₂R, and an optionally substituted group selected from C₁₋₈ aliphatic, aryl, aralkyl, heterocyclyl, heterocycloalkyl, heteroaryl, and heteroaralkyl, or two ortho R⁴s, taken together with the ortho carbon atoms to which they are bonded, form an optionally substituted five or six membered phenyl, pyridyl or heterocyclyl fused to Ring A;

each R⁵ is independently selected from hydrogen, C₁₋₆ aliphatic, —CO₂R, —SO₂R, and —C(O)R, or two R⁵ on the same nitrogen taken together with the nitrogen form a 5–8 membered heteroaryl or heterocycle ring having 1–4 heteroatoms selected from N, O, and S;

each R⁸ is independently a C₁₋₃ alkyl or, taken together with the nitrogen atom to which they are bonded, a 5–7 membered nitrogen containing heterocycle;

Ring D is optionally substituted by C₁₋₄ aliphatic or haloaliphatic, —OR⁷, —SR⁷, —C(O)R⁷, —CO₂R⁷, —SO₂R⁷, —CN, —C(O)N(R⁷)₂, —N(R⁷)C(O)C₁₋₂alkyl), or —N(R⁷)₂, and is optionally fused to an optionally substituted phenyl or optionally substituted cyclohexyl ring;

each R⁷ is independently selected from hydrogen or an optionally substituted C₁₋₃ aliphatic or —N(R⁷)₂ is a nitrogen-containing heterocyclyl;

each R is independently selected from hydrogen and an optionally substituted group selected from C₁₋₆ aliphatic, aryl, aralkyl, heteroaryl, and heteroaralkyl-butyl; and Rˣ is C1–C8 alkyl.

2. The compound of claim 1 wherein R² and R³ are each hydrogen, and Z is oxygen.

3. The compound of claim 2 wherein V is —O— and T is C₂₋₅ alkylidene.

4. The compound of claim 3 wherein the compound is represented by the following structural formula:

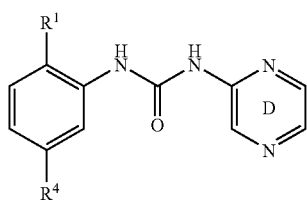

or a pharmaceutically acceptable salt thereof, wherein:

R⁴ is —F, —Cl, —Br, —I, —COORᵃ, —NHCORᵃ, —CF₃, —CH₃, —CH₂CH₃, —CH(CH₃)₂, —N(Rᵃ)₂, —CH₂N(Rᵃ)₂, —CH₂CH₂N(Rᵃ)₂, piperidinyl, morpholinyl or pyrrolidinyl;

Rᵃ is —CH₃, —CH₂CH₃, —CH₂CH₂NH₂, —CH₂CH₂NH(CH₃), —CH₂CH₂N(CH₃)₂, —CH₂CH₂(N-morpholinyl), —CH₂CH₂(N-piperidinyl) or —CH₂CH₂(N-pyrrolidinyl); and Ring D is optionally monosubstituted at the position meta or para to the carbon atom bonded to the urea nitrogen with methyl, —OCH₃, or —NH₂, and is optionally fused to a phenyl or cyclohexyl ring.

5. The compound of claim 3 wherein the compound is represented by the following structural formula:

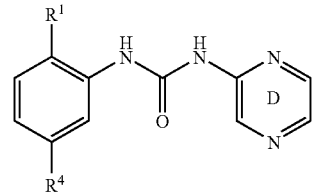

or a pharmaceutically acceptable salt thereof, wherein:

R⁴ is —F, —Cl, —Br, —I, —COORᵃ, —NHCORᵃ, —CF₃, —CH₃, —CH₂CH₃, —CH(CH₃)₂, —N(Rᵃ)₂, —CH₂N(Rᵃ)₂, —CH₂CH₂N(Rᵃ)₂, piperidinyl, morpholinyl or pyrrolidinyl;

Rᵃ is —CH₃, —CH₂CH₃, —CH₂CH₂NH₂, —CH₂CH₂NH(CH₃), —CH₂CH₂N(CH₃)₂, —CH₂CH₂(N-morpholinyl), —CH₂CH₂(N-piperidinyl) or —CH₂CH₂(N-pyrrolidinyl); and Ring D is optionally monosubstituted at the position para to the carbon atom bonded to the urea nitrogen with —CO₂R⁷, —CN or —C(O)N(R⁷)₂.

6. The compound of claim 3 wherein R¹ is —(C₂₋₅ alkylidene)-NH₂ or —O—(C₂₋₅ alkylidene)-NH₂.

7. A compound represented by a structural formula selected from the group consisting of:

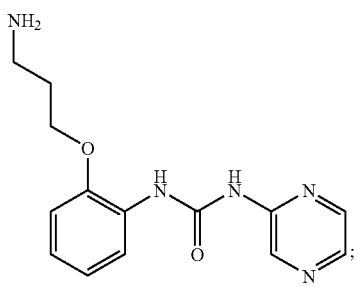

-continued
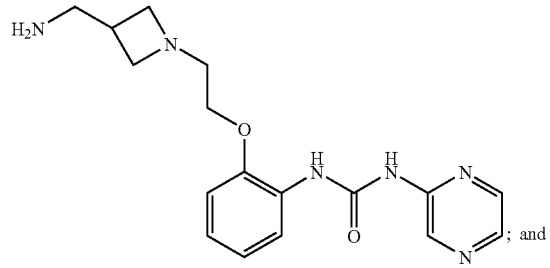
; and
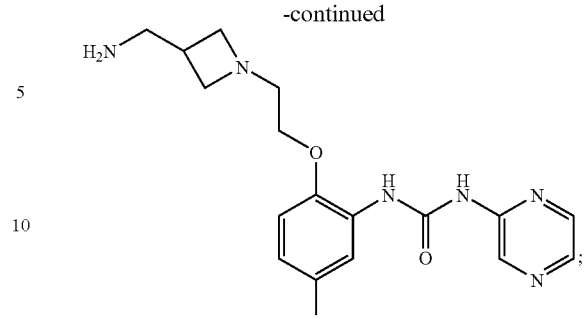
or a pharmaceutically acceptable salt thereof.
* * * * *